US006773889B2

(12) United States Patent
Cullis et al.

(10) Patent No.: US 6,773,889 B2
(45) Date of Patent: Aug. 10, 2004

(54) METHOD FOR DETECTING GENOMIC DESTABILIZATION ARISING DURING TISSUE CULTURE OF PLANT CELLS

(75) Inventors: Christopher A. Cullis, Shaker Heights, OH (US); Samantha Rademan, Kempton Park (ZA); Karl Kunert, Randburg (ZA)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 10/193,451

(22) Filed: Jul. 11, 2002

(65) Prior Publication Data

US 2003/0096269 A1 May 22, 2003

Related U.S. Application Data

(63) Continuation of application No. 09/292,646, filed on Apr. 15, 1999, now Pat. No. 6,500,616.
(60) Provisional application No. 60/081,975, filed on Apr. 16, 1998.

(51) Int. Cl.[7] .............................. C12Q 1/68; C12Q 1/44; C12P 19/34; C12N 5/02
(52) U.S. Cl. ............................ 435/6; 435/19; 435/91.2; 435/410
(58) Field of Search ............................. 435/6, 19, 91.2, 435/410

(56) References Cited

U.S. PATENT DOCUMENTS

| | | | |
|---|---|---|---|
| 5,324,631 A | 6/1994 | Helentjaris et al. | 435/6 |
| 5,385,835 A | 1/1995 | Helentjaris et al. | 435/172.3 |
| 5,424,483 A | 6/1995 | Pfund et al. | 800/200 |
| 5,436,142 A | 7/1995 | Wigler et al. | 435/91.2 |
| 5,444,177 A | 8/1995 | Pfund et al. | 800/200 |
| 5,476,524 A | 12/1995 | Leon et al. | 47/58 |
| 5,500,361 A | 3/1996 | Kinney | 435/172.3 |
| 5,501,964 A | 3/1996 | Wigler et al. | 435/91.2 |
| 5,602,310 A | 2/1997 | Petolino | 800/200 |
| 5,648,210 A | 7/1997 | Kerr et al. | 435/6 |
| 5,650,559 A | 7/1997 | Akamatsu et al. | 800/220 |
| 5,689,035 A | 11/1997 | Webb | 800/200 |
| 5,876,929 A | 3/1999 | Wigler et al. | 435/6 |
| 6,500,616 B1 * | 12/2002 | Cullis et al. | 435/6 |

FOREIGN PATENT DOCUMENTS

| | | |
|---|---|---|
| EP | 0 534 858 | 3/1993 |
| EP | 0 537 178 | 8/1994 |
| EP | 0 552 393 | 5/1997 |
| EP | 0 804 618 | 1/1999 |
| JP | 4262798 | 9/1992 |
| JP | 7059577 | 3/1995 |
| JP | 7087979 | 4/1995 |
| JP | 9271399 | 10/1997 |
| WO | WO 84/07647 | 8/1989 |
| WO | WO 92/18646 | 10/1992 |
| WO | WO 94/11383 | 5/1994 |
| WO | WO 95/27081 | 10/1995 |
| WO | WO 96/21010 | 7/1996 |
| WO | WO 97/37042 | 10/1997 |
| WO | WO 98/14607 | 4/1998 |
| WO | WO 99/53100 | 10/1999 |

OTHER PUBLICATIONS

Annholdt–Schmitt, B. et al., (1995). Physiological aspects of genome variability in tissue culture. I. Growth phase–dependent differential DNA methylation of the carrot genome (*Daucus carota* L.) during primary culture. *Theoret. Appl. Genet.* 91, 809–815.

Bogani, P. et al. (1995). Genome flux in tomato auto– and auxo–trophic cell clones cultured in different auxin/cytokinin aquilibria. I. DNA multiplicity and methylation levels. *Genome* 38, 902–912.

Carver, B.F. and B.B. Johnson (1989). Partitioning of variation derived from tissue culture of winter wheat. *Theoret. Appl. Genet.* 78, 405–418.

Crouch, J.H. et al. (1998). Perspectives on the application of biotechnology to assist the genetic enhancement of plantain and banana (*MUSA* spp.). *EJB Electronic Journal of Biotechnology* 1, 1–12.

Cullis, C.A. (1977). Molecular aspects of the environmental induction of heritable changes in flax. *Heredity* 38, 129–154.

Cullis, C.A. (1979). Quantitative variation of ribosomal RNA genes in flax genotrophs. *Heredity* 42, 237–246

Cullis, C.A. (1991). The Molecular Biology of Plant Cells and Cultures in Comprehensive Biotechnology. M.W. Fowler and G.S. Warren, eds.

Damasco, O. et al. (1996). *Plant Cell Rep.* 16, 118–122.

Donnison, I.S. et al. (1996). Isolation of Y chromosome–specific sequences from *Silene Iatifolia* and mapping of male sex determining genes using Representational Difference Analysis. *Genetics* 144, 1893–1901.

Engelborghs, I. et al., (1998). The potential of AFLP to detect genetic differences and somaclonal variants in *Musa* spp. *INFOMUSA* 7, 3–7.

(List continued on next page.)

*Primary Examiner*—Diana B. Johannsen
(74) *Attorney, Agent, or Firm*—Jones Day

(57) ABSTRACT

The invention provides a method for obtaining molecular markers for use as a diagnostic and quality control tool to identify genomic polymorphisms that arise during the process of tissue culture of in vitro propagated plants. By using a representational difference analysis (RDA) adapted for plant genomes, a set of nucleic acid difference sequences between normal and off-type plant genomes are obtained. The invention further provides a method for isolating sets of variant sequences which are common to many naturally occurring or tissue culture-generated off-types of the same cultivar or species, in addition to variant sequences present in all off-types, regardless of the phenotypic mutation, and/or in all off-types that exhibit the same mutation. Detection of somaclonal variation by the method of the invention may present an opportunity to optimize tissue culture conditions and to optimize plant multiplication rates without producing a significant number of off-types.

22 Claims, 4 Drawing Sheets

OTHER PUBLICATIONS

Giorgetti, L. et al. (1995). On the occurrence of somatic meiosis in embryogenic carrot cell cultures. *Mol. Gen. Genet.* 246, 657–662.

Ho, P.J. et al (1996). *Blood* 87(3), 1170–1178.

Ilan A. and E. Khayat (1997). An overview of commercial and technological limitations to marketing of micropropagated plants. *Acta Hort.* 447, 643–648

Israeli, Y. et al. (1991). Qualitative aspects of somaclonal variations in banana propagated by in vitro techniques. *Scientia Hortic.* 48, 71–88.

Israeli, Y. et al. (1996). Selection of stable banana clones which do not produce dwarf somaclonal variants during in vitro culture. *Scientia Hortic.* 67, 197–205.

Kaeppler, S.M. and R.L. Phillips (1993). Tissue culture–induced DNA methylation variation in maize. *Proc. Natl. Acad. Sci. USA* 90, 8773–8776.

Karp, A. and E.C. Bridge (1993). Are your plants normalf— Genetic instability in regenerated and transgenic plants. Agro–Food–Industry Hi–Tech, May/Jun. 1993, pp. 7–12.

Karp, A. (1991). On the current understanding of somaclonal variation. *Oxford Surveys of Plant Molecular and Cell Biology* 7, 1–58

Larkin, P.J. and W.R. Scowcroft (1981). Somaclonal variation—a novel source of variability from cell cultures for plant improvement. *Theor. Appl. Genet.* 60, 197–214.

Lee, M. and R.L. Phillips (1988). The chromosomal basis of somaclonal variation. *Ann. Rev. Plant Physiol. Mol. Biol.* 39, 413–437.

Lin, J.j. and J. Kuo (1995). AFLP: A novel PCR–based assay for plant and bacterial fingerprinting. *Focus* 17, 66–72.

Lisitsyn, N., Lisitsyn, N. and M. Wigler (1993). Cloning the differences between two complex genomes. *Science* 259, 946–951.

Listisyn, N. et al. (1994). Direct isolation of polymorphic markers linked to a trait by genetically directed representational differences analysis. *Nature Genetics* 6, 57–63.

Lisitsyn, N. et al. (1995). Comparative genomic analysis of tumors: detection of DNA losses and amplifications. *Proc. Natl. Acad. Sci. USA* 92, 151–155.

Michiels, L. et al. (1998). Representational difference analysis using minute quantities of DNA. *Nucleic Acids Research* 26, 3608–3610.

Morere–Le Pavan, et al. (1992): Organ/tissue–specific changes in mitochondrial genome organization of in vitro cultures derived from different explants of a single wheat variety. *Theoret. Appl. Genet.* 85, 1–19.

Phillips, R.L. et al. (1990). Do we understand somaclonal variationf in Progress in Plant Cellular and Molecular Biology. pp. 136. Nujkamp, H.J.J. et al., eds. Kluwer Academic Publishers, Netherlands.

Rani, V. et al. (1995). Random amplified polymorphic DNA (RAPD) markers for genetic analysis in micropropagated plants of *Populus deltoides* Marsh. *Plant Cell Reports* 14, 459–462.

Reuveni, O. and Y. Israeli (1990). Measures to Reduce Somaclonal Variation in In Vitro Propagated Bananas. *Acta Horticulturae* 275, 307–313.

Rival, A. et al. (1998). Suitability of RAPD analysis for the detection of somaclonal variants in oil palm. *Plant Breeding* 117, 73–76.

Roth, E.J. et al. (1989). Genetic variation in an inbred plant: variation in tissue culture of soybean (Glycine max (L.) Merrill). *genetics* 121, 359–368. 777.

Shchukin, A. et al. (1997). Plant regeneration via somatic embryogenesis in *Grand Nain* banana and its effect on somaclonal variation. *Acta Hort.* 447, 317–318.

Smulders, M.J.M. et al.(1995). Tissue culture–induced DNA methylation polymorphisms in repetitive DNA of tomato calli and regenerated plants *Theoret. Appl. Genet.* 91, 1257–1264.

Straus D. & F.M. Ausubel (1990). Genomic subtraction for cloning DNA corresponding to deletion mutations. *Proc. Natl. Acad. Sci. USA* 87, 1889–1893.

Taylor, P.W.J. et al. (1995). Sensitivity of random amplified polymorphic DNA analysis to detect genetic change in sugarcane during tissue culture. *Theor. Appl. Genet.* 90, 1169–1173.

Ushijima, T. et al. (1997). Establishment of methylation–sensitive–representational difference analysis and isolation of hypo——hypermethylated genomic fragments in mouse liver tumors. *Proc. Natl. Acad. Sci. USA* 94, 2284–2289.

Vuylsteke, D.R. et al. (1998). The biotechnology case history for MUSA. *Acta Hort.* 461, 75–86.

Walbot, V. and C.A. Cullis (1985). Rapid genomic changes in higher plants. *Ann. Rev. Plant Physiol.* 36, 367–396.

Walther, R. et al. (1997). Analysis of somaclonal variation in tissue cultured banana plants (MUSA AAA cv.'Grand Nain'). *Acta Hort.* 447, 379–383.

Williams, J.G.K. et al. (1990). DNA polymorphisms amplified by arbitrary primers are useful as genetic markers. *Nuc. Acids Res.* 1s, 6531–6535.

Yoshida, Y. et al. (1999). Development of the arbitrarily primed–representational difference analysis method and chromosomal mapping of isolated high throughout rat genetic markers. *Proc. Natl. Acad. Sci. USA* 96, 610–615.

Levall, M.W. et al. (1995) Molecular characterization of UV–treated sugar beet somaclones using RFLP markers. *Physiol. Plant.* 90(1): 216–220.

Landsmann, J. et al. (1985) Somaclonal variation in solanum–tuberosum detected at the molecular level. *Theor. Appl. Genet.* 71(3): 500–505.

\* cited by examiner

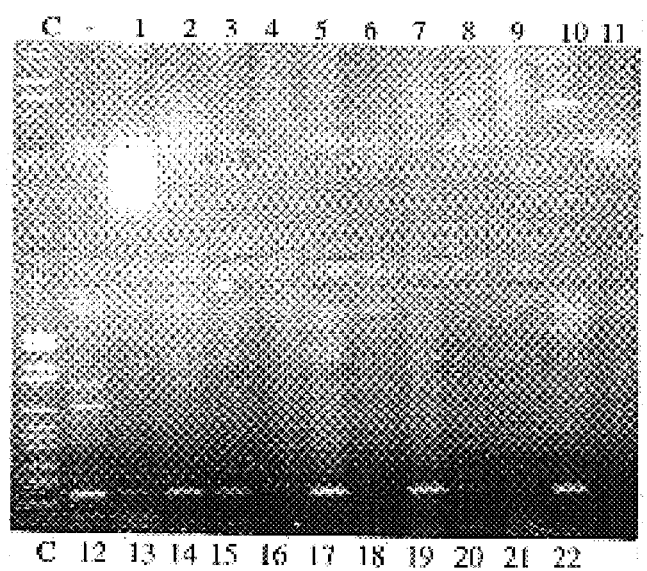
Figure 1 (upper)
Figure 2 (lower)

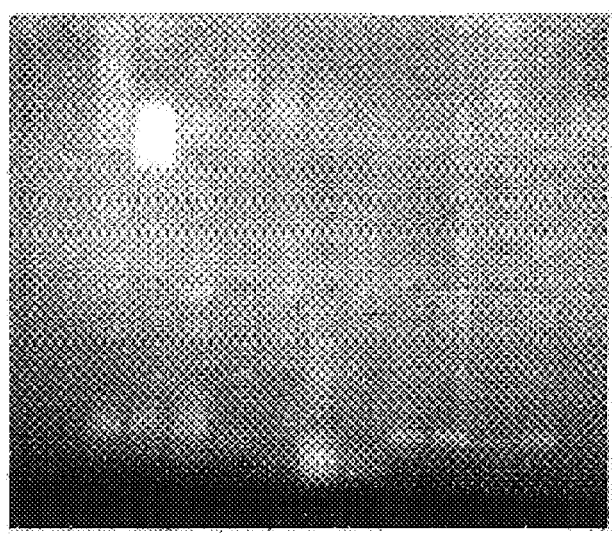
Figure 3 (upper)
Figure 4 (lower)

METHOD FOR DETECTING GENOMIC DESTABILIZATION ARISING DURING TISSUE CULTURE OF PLANT CELLS

This application is a continuation of prior U.S. patent application Ser. No. 09/292,646, filed Apr. 15, 1999, now U.S. Pat. No. 6,500,616, which claims the benefit of U.S. Provisional Patent Application Serial No. 60/081,975, filed Apr. 16, 1998. The entire disclosure, of U.S. Ser. No. 09/292,646 is hereby incorporated herein by reference.

BACKGROUND OF THE INVENTION

The invention relates to the isolation of molecular markers of genetic mutation in plants by representational difference analysis (RDA). In particular, the invention relates to the preparation of genetic probes for early identification of plants that are not true-to-type. More particularly, the invention relates to the use of such genetic probes as a diagnostic and quality control tool for monitoring the development of genetic polymorphisms arising during tissue culture regeneration of plants.

The large-scale production of commercially elite plants by in vitro micropropagation is technically available for a number of species. A common problem encountered when growing plants by tissue culture is the development of tissue culture-induced genomic polymorphisms in which genetic changes in the nuclear, mitochondrial and/or chloroplast genomes result in a lack of homogeneity among the regenerants and the production of inferior plants that are not true-to-type (i.e., "off-type" plants) with little commercial value. The development of genetic polymorphisms in tissue culture is termed "somaclonal variation". As used herein, the term "off-type" refers to a plant that exhibits a phenotypic difference from a normal plant.

Investment in plants that are later discovered to be off-types can have severe financial implications for both growers and plant producers, who may only discover that the plants are off-types after the plants have grown for some period of time in the field. Traditionally, an experienced examiner is required to identify off-type plants by a morphological description and visual monitoring of plant characteristics. However, many characteristics are only expressed in a more mature stage of plant development and not in in vitro plants or very young plants. For example, in banana plants, off-types such as dwarfs, mosaics (which have irregular bright yellow spots or stripes on the leaf) and masadas (which have abnormal foliage showing depressions and thicker leaves) are difficult to identify at both the tissue culture and nursery stages [Israeli et al. (1991) *Scientia Hortic.* 48, 71–88]. Therefore, a method for early monitoring and identification of off-type plants, while still at the tissue culture or nursery stages, would be a very advantageous tool to enable the selection of desired true-to-type plants for further propagation.

Attention was first drawn to somaclonal variation by Larkin and Scowcroft [*Theoret. Appl. Genet.* 60,197-24 (1981)] and a great deal of literature on the subject has accumulated [see reviews by M. Lee and R. L. Phillips, *Ann. Rev. Plant Physiol. Mol. Biol.* 39, 413–437 (1988); R. L. Phillips et al., in Progress in Plant Cellular and Molecular Biology, Kluwer Academic Publishers, Netherlands, pp. 136 (1990); C. A. Cullis, The Molecular Biology of Plant Cells and Cultures in Comprehensive Biotechnology, M. W. Fowler and G. S. Warren, eds., Pergarmmon Press, NY (1991); A. Karp, *Oxford Surveys Plant Mol. Cell. Biol* 7, 1–58 (1991)]. A large number of variants in morphological and biochemical characteristics, as well as in changes at the DNA level, have been characterized. At the genomic level, changes in ploidy level, chromosomal rearrangements, activation of transposable elements, gene amplification, single gene mutations and variation in quantitative traits have been reported. Variations in mitochondrial and chloroplast genomes in regenerants, particularly in cereals, have also been reported [M. D. Morere-Le Pavan et al. *Theoret. Appl. Genet.* 85, 1–19 (1992)], thus illustrating that all compartments of the genetic information of the plant cell are susceptible to the phenomenon of somaclonal variation. In addition to the alterations in genomic DNA sequence and organization, stable changes in nucleic acid methylation patterns have been implicated as a major factor in epigenetic changes [S. M. Kaeppler and R. L. Phillips, *Proc. Natl Acad. Sci. USA* 90, 8773–8776 (1993); M. J. M. Smulders et al., *Theoret. Appl. Genet* 91, 1257–1264 (1995); B. Arnholdt-Schmitt et al., *Theoret. Appl. Genet.* 91, 809–815 (1995); P. Bogani et al., *Genome* 38, 901–912 (1995)]. The question of how and when during the tissue culture process variations occur has also been addressed. A study in wheat indicated that the variation in these cultures originated during the callus phase and that the extent of variation could be affected by manipulation of the culture medium [B. F. Carver and B. B. Johnson, *Theoret. Appl. Genet.* 78, 405–418 (1989)].

A series of PCR (polymerase chain reaction) based technologies have been used by investigators to compare and highlight the differences between DNAs isolated from related sources. For example, restriction fragment length polymorphisms (RFLP) have been used, particularly by plant breeders, as genetic markers in developing genetic linkage maps in which chromosomal regions associated with desirable phenotypic traits may be identified and tracked during subsequent selective breeding to produce improved plant lines. RFLPs are genetic differences detectable by DNA fragment lengths, typically revealed by agarose gel electrophoresis after restriction endonuclease digestion of DNA. There are large numbers of restriction endonucleases available, characterized by their nucleotide cleavage sites and their source, e.g., the bacteria *E. coli*. Variations in RFLPs result from nucleotide base pair differences which alter the cleavage sites of the restriction endonucleases, or by insertions, yielding different sized fragments. Other point mutations in the genome usually go undetected. Thus, RFLP differences often are difficult to identify. Although RFLP has advantages in detecting genetic variation, it is labor intensive.

Sequence tagged sites (STS) of DNA polymorphisms have been developed by the use of RFLP. However, the development of STS requires an already identified difference which can be tested for in the unknown cell lines. Thus, STS is not a useful approach to isolate differences between uncharacterized cultivars.

Random amplified polymorphic DNAs (RAPD) and amplified fragment length polymorphisms (AFLP) are two further techniques that simply compare the DNA from any number of different samples and can be used to detect the level of difference between them. The RAPD method employs DNA amplification by PCR using short primers of arbitrary sequence (random amplified polymorphic DNA). Differences as small as single nucleotides between genomes can affect the RAPD primer's binding/target site, and a PCR product may be generated from one genome but not from another. RAPD detection of genetic polymorphisms represents an advance over RFLP in that it is less time consuming, more informative, and readily adaptable to automation. However, RAPD is limited in that only dominant polymorphisms can be detected (i.e., this method does not offer the ability to examine simultaneously all the alleles at a locus in a population). However, because of its sensitivity for the detection of polymorphisms, RAPD method has been widely used for analyzing genetic variation within species or closely related genera, both in the animal and plant kingdoms. In particular, RAPD has been used by several groups for off-type plant detection and, recently, a potential RAPD marker has been identified for a dwarf banana off-type [O. Damasco et al., Plant Cell Rep. 16, 118–122 (1996)]. However, this use of the RAPD technique was restricted to attempting to generate a marker for dwarfism, with no reference made to attempting to find generalized markers of polymorphism. Both RFLP and RAPD have been used to distinguish between regenerants from embryogenic carrot cell lines [L. Georgetti et al., Mol. Gen. Genet. 246, 657–662 (1995)]. The RAPD technique however, generally has several disadvantages, including a lack of reproducibility of results and the necessity of using of a large number of different primers to detect variation in only a small portion of the genome.

AFLP is similar in concept to RFLP in that restriction enzymes are used to specifically digest the genomic DNA to be analyzed. The primary difference between RAPD and AFLP is that the amplified restriction fragments produced in AFLP are modified by the addition of specific, known adaptor sequences which serve as the target sites for PCR amplification with adaptor-directed primers. In both RAPD and AFLP, however, only those differences specific to a particular primer, or primer set, are detected in any one reaction. Therefore, if the material is only different at a few sites within the genome (that is, the samples are closely related) a large number of primers must be used in order to detect variation. For example, in experiments we conducted with flax, the use of 300 different RAPD primers only covered about one percent of the genome.

Another known PCR-based technology is simple sequence repeat polymorphisms (SSR). The SSR method of assaying polymorphisms involves utilizing the high degree of length variation resulting from certain repeating nucleotide sequences (simple sequence repeats) found in most genomes. SSR polymorphisms can be detected by PCR using minute amounts of genomic DNA and, unlike RAPDs, they can detect a high degree of genetic polymorphism. Although SSR has been used successfully for comparative analysis and mapping of mammalian and plant genomes, there are practical drawbacks to the method. The markers generated by the method are obtained by first constructing a genomic library, screening the library with probes representing the core elements of a particular repeat sequence, purifying and sequencing the positive clones, and synthesizing the primers specific for the flanking sequences for each cloned SSR locus. Genomic DNA is then amplified to screen for polymorphisms, and mapping of the genome is then carried out. The entire process is time consuming, expensive and technically demanding.

An alternative method for detecting nucleic acid sequences present in one but absent from another population of otherwise similar nucleic acid sequences is the technique of subtractive hybridization. For the purposes of this technique, the two genomic populations are called tester DNA and driver DNA, respectively. The basic rationale of subtractive hybridization is to compare two DNAs by using the driver DNA in excess during hybridization with the tester DNA to remove (subtract) all of the sequences held in common between the two DNA samples. Therefore, what are left are those sequences which vary between the two DNA samples. The technique thus enriches for a set of (target) sequences that are unique to the tester DNA.

In one reported method of subtractive hybridization, a physical difference (e.g., a label, such as biotin) between the driver and tester DNAs is introduced prior to allowing the two DNAs to hybridize. The desired (unique) tester sequences are segregated from the unwanted (common) tester sequences by a strategy in which, during the hybridization step, driver DNA is provided in excess over the tester DNA so that most of the sequences common to tester and driver populations form tester-driver duplexes. Thus, sequences common to both populations segregate with the driver DNA when the physical difference is exploited after the hybridization step to separate the tester from the driver DNA (e.g., biotin containing duplexes are removed by binding to strepavidin coated beads). In the simplest form of subtractive hybridization, driver DNA is prepared for hybridization by methods that produce random ends (e.g., sonication or mechanical shearing), while tester is prepared by restriction endonuclease digestion that facilitates its later ligation into cloning vectors.

Representational Difference Analysis (RDA) belongs to the general class of subtractive methodologies in which subtractive hybridization and PCR are combined, and is a reliable way to detect differences between two complex genomes. [Lisitsyn et al., Science 259, 946 (1993); Lisitsyn et al., Nature Genetics 6, 57–63 (1994); U.S. Pat. No. 5,436,142]. RDA does not require the use of any label, such as biotin, nor any post-reassociation physical separation techniques. However, for complex DNAs, such as mammalian DNAs having about $10^9$ base pairs (bp), it is necessary to reduce the complexity of the hybridizing mixture for the subtractions to be efficient. The reduction in complexity can be achieved by any method which reproducibly generates a subpopulation of the genome. Lisitsyn et al. prepared representations (amplicons) of the two genomes to be compared by digesting the genomic DNAs with a restriction endonuclease that recognizes a six-base sequence, and using PCR to amplify the total digestion product after ligating a universal adaptor. Restriction fragments whose sizes and sequences were suitable for PCR amplification were enriched in the amplicons, and other fragments remained unamplified. This procedure resulted in a population of relatively short fragments that represented substantially fewer sequences than were present in the initial DNA populations. The term "representational" in RDA, therefore, refers to the production of a reproducible subpopulation of DNA fragments having a complexity that may be only between 1% and 12% of the starting population. Thus, a disadvantage of the representation step of RDA is that only a very small portion of the entire genome is tested and only some part of all the differences existing between the two DNAs will be detected.

The afore-mentioned technologies for comparing differences between DNAs isolated from related sources have been used to isolate or track phenotypically-expressed variant-specific markers in plant genomes, such as markers for dwarfism in bananas, galactinol synthase in soybean seed and zucchini leaf, height in tomatoes, β-ketoacyl-ACP synthetase II in soybean, cotton, tomato and tobacco, high seed oil production in sunflowers, brown stem rot resistance in soybeans, and the like. However, there are no known reports of employing any of these technologies to isolate and identify a set of genetic markers that can be used to detect and/or identify genomic polymorphisms as they arise during the course of plant tissue culture.

SUMMARY OF THE INVENTION

The present invention takes advantage of the strategy of representational difference analysis (RDA) in a method for obtaining molecular markers for use as a diagnostic and quality control tool to identify genomic polymorphisms that arise during the in vitro process of tissue culture of vegetatively propagated plants. The invention is based on the premise that there is a labile fraction of the plant genome which is altered whenever a somaclonal variant is observed. That is, that there are sites within the genome of normal plants which are especially labile and may be altered due to environmental stresses, particularly stresses induced by tissue culture, often without any specific phenotypic mutation being observable in the resulting plants. Thus, genomic polymorphisms may occur that are "silent" in the regenerated plant, but are indicative of changes which have occurred due to environmental stresses.

In one embodiment, the invention provides a method for identifying genomic polymorphisms arising during the process of tissue culture of plant cells, comprising the steps of isolating DNA from (i) a normal plant, and (ii) an off-type plant of the same species; performing RDA to obtain a DNA subtraction product representing a genetic difference between the off-type plant DNA and the normal plant DNA; isolating DNA from a sample of plant cells in tissue culture; and using the DNA subtraction product to identify a putative DNA sequence difference between the DNA from the sample of plant cells in tissue culture and the DNA from the normal plant; wherein, if no DNA sequence difference is identified, the method further comprises repeating the identification step on further samples of plant cells isolated at subsequent time intervals during the tissue culture process and repeating the identification using the DNA subtraction product until a DNA sequence difference is identified or until the tissue culture process is completed.

The method preferably further comprises the step of amplifying the DNA subtraction product to obtain a probe comprising a nucleic acid sequence containing the genetic difference, for use in the identification step. By the method of the invention, a plurality of DNA subtraction products may be isolated from a single off-type plant and/or from a plurality of off-type plants, and individual probes obtained that form a library of genetic difference probes for use in identifying somaclonal variants.

The identification of a genetic polymorphism arising in a tissue culture may be indicative of culture conditions that are environmentally stressful to the cells. Thus, if such a genetic polymorphism is identified during tissue culture, the method preferably further comprises the step of adjusting tissue culture conditions (e.g., nutrient enrichment, pH adjustment, hormone type and/or concentration adjustment, cytokinin type and/or concentration adjustment, and the like) to optimize the conditions to alleviate environmental stresses and to prevent the occurrence of further somaclonal variation in the culture. Thus, an advantage of the method of the invention is that it affords the opportunity to develop criteria for optimum tissue culture conditions for propagating a given plant cell species or cultivar in vitro, and to optimize plant multiplication rates without producing a significant number of off-types.

In another embodiment of the invention, a method is provided for isolating markers of genomic integrity of plants. As used herein, "markers of genomic integrity" are intended to mean normal nucleic acid sequences that have not undergone somaclonal variation. Thus, in this embodiment of the method, RDA is performed using an off-type plant DNA as driver DNA and a normal plant DNA as tester DNA, to obtain a DNA subtraction product representing a DNA sequence present in the normal plant and not present in the off-type plant. Preferably, the driver DNA is from a pool of off-type plants representing a plurality of different phenotypic mutations, in order to isolate a plurality of DNA sequences present in the normal plant that may show particular lability due to environmental stresses encountered in tissue culture. These DNA subtraction products may then be used as probes to monitor the genetic stability of plant cells during the process of tissue culture. Moreover, this embodiment of the method of the invention provides markers for genomic integrity that are useful in selecting particular individual plants for use as founding members of breeding lines, especially in the generation of transgenic lines.

In other embodiments, the invention provides methods for isolating one or more markers of representing genomic alterations that are common to a plurality of different off-type plants, and markers that represent specific genomic alterations associated with a particular phenotypic mutation. An advantage of these methods of the invention is that markers are provided that may be used to identify a gene or combination of genes in the normal genome that code for specific phenotypes, and sequence tagged sites may be developed. Moreover, by the methods of the invention, difference products may be isolated by RDA between plants exhibiting desirable traits and plants exhibiting undesirable traits. Genetic markers thus isolated will represent specific phenotypic mutations, which may be used to identify and isolate genes for desirable traits, such as disease or pest resistance, for use in generating transgenic plant lines having such desirable traits.

The methods of the invention for identifying and monitoring genomic polymorphisms arising during tissue culture allow early identification of regenerant plants that may remain phenotypically "normal" but still express variant nucleic acid sequences on a molecular level. The invention methods further allow early identification of regenerant plants that express variant nucleic acid sequences associated with a specific mutation, prior to the actual phenotypic expression of the mutation. Moreover, by the methods of the invention, the degree to which a phenotypic variation may be expressed in the regenerants from the plant tissue culture can be estimated (e.g., as a percentage). The invention thus provides two different types of molecular markers, one of which is indicative of variations occurring progressively from very early to late time stages of tissue culture, and the second which is specific to a particular phenotypic off-type. Plants which have "silent" polymorphisms, but are phenotypically normal, are usually commercially acceptable, and tissue cultures containing such plant cells are not necessarily discarded; but the presence of these polymorphisms may indicate unstable culture conditions which may require adjustment, as described above. The identification during tissue culture of a genetic polymorphism associated with a marker specific to an undesirable off-type plant is likely to result in discard of the culture. Thus, the methods of the invention provide, not only a diagnostic tool, but a quality control tool for micropropagation of plants.

In addition to the advantages of the invention described above, the characterization of genes and the genomic locations involved in the generation of somaclonal variations is expected to aid in the understanding the genomic mechanisms involved in control of a rapid genomic response to environmental stresses in plants.

BRIEF DESCRIPTION OF THE DRAWINGS

FIGS. 1 and 2 illustrate side by side agarose gel electrophoreses of PCR amplifications of DNAs from various banana cultivars, using the primer pair developed from the genetic probe Hpa-15, generated as a DNA difference product by RDA between a normal banana cultivar (Williams) and an off-type cultivar (#3). The first lane in each Figure is a molecular weight marker. The remaining lanes are as follows: (–), no DNA control; lanes 1–4, independent extraction of Williams leaves; lanes 5–10, various samples of other normal cultivars FIHA1 (lanes 5 and 6), FIHA 21 (lanes 7 and 9), FIHA 3 (lane 8) and Yangambi (lane 10); Grand Nain cultivars (lanes 11, 12 and 13); dwarf Grand Nain off-types (lanes 14 and 15); lanes 17–22, previously identified off-types of the Williams cultivar (lanes 17–22).

FIGS. 3 and 4 illustrate the same DNAs as in FIGS. 1 and 2, amplified with a primer pair developed from the genetic probe, Hpa-5, generated as a DNA difference product by RDA between the normal banana cultivar, Williams, and the off-type cultivar, #3.

In FIG. 6A, the lanes represent the following: M, the molecular weight marker VI (Boehringer Manheim); amplicons of normal P1(1), and the off-types $L_6$ (2), $S_6$ (3), $C_2$ (4) and $L_H$ (5), a mixture of 2, 3, 4 and 5 (6); first (7), second (8) and third (9) round subtractions of P1 (tester) and the mixture (6) (driver). FIG. 6B illustrates the gel of FIG. 6A transferred by blotting to a nitrocellulose filter and hybridized with a fluorescein-labeled cloned subtraction product, probe 4-2, obtained by RDA.

DETAILED DESCRIPTION OF THE INVENTION

Figure 5:
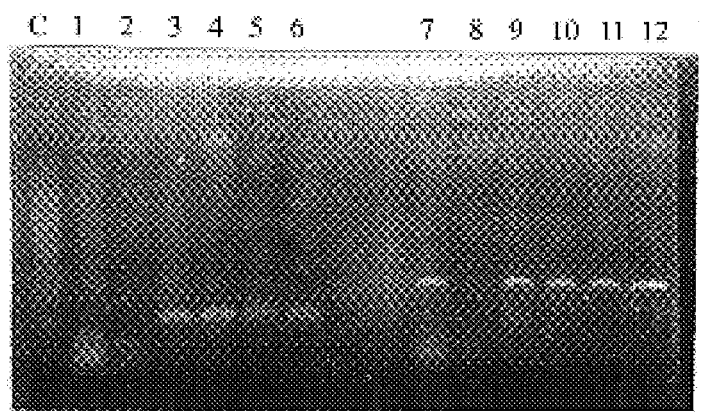
FIG. 5 illustrates a repeat amplification of the off-type DNAs in lanes 17–22 of FIGS. 1–4, using the primer pair developed from the Hpa-5 probe (lanes 1–6) and the Hpa-15 probe (lanes 7–12). Lane "C" is the no DNA control.

Embodiments of the invention provide methods for isolating markers of genetic polymorphisms and markers of genomic integrity in plants by adapting the technique of representational difference analysis (RDA) to plant genomes. The invention further provides methods for using such markers to detect somaclonal variation arising during tissue culture regeneration of plants. The identification of a genetic polymorphism arising in a tissue culture, by the methods of the invention, may be indicative of culture conditions that are environmentally stressful to the cells. For example, tissue culture stresses may be induced by factors including, but not limited to, a change in pH (which may be about 5.8 at the beginning of culture, but may drop to as low as 4.0 after a period of time), the level of nutrients including minerals in the tissue culture medium, the presence and/or concentration of hormones such as 2,4-dichlorophenoxyacetic acid (2,4-D), and the presence and/or concentration of cytokinins such as 6-benzyl-aminopurine (BAP), and the like. Thus, if a genetic polymorphism is identified during tissue culture, the method preferably further comprises the step of adjusting tissue culture conditions (e.g., nutrient enrichment, pH adjustment, hormone type or concentration adjustment, cytokinin type or concentration adjustment, and the like) to optimize the conditions to alleviate environmental stresses and to prevent the occurrence of further somaclonal variation in the culture.

The methods of the invention may be used for any type of plant that can be vegetatively propagated, including vegetable and cereal crops, grasses, ornamental plants, trees, and the like. The invention is particularly useful during vegetative propagation of important food and industrial crops, especially those of tropical and subtropical plants, such as bananas, oil palms, date palms, pineapples, plantain, papaya, flax, sugar cane, rhododendron, eucalyptus, coffee, and the like, as well as in the generation of transgenic plants, which usually pass through a tissue culture stage.

In order to increase the probability of finding the majority of sequence differences between uncharacterized closely-related plants of a single species or cultivar, it is preferred that a number of different restriction endonucleases that recognize different cutting site-sequences are used to prepare amplicons. The use of more than one enzyme increases the likelihood of revealing sequence differences that might be otherwise be masked if only a single restriction enzyme were to be used. The methods of the invention preferably further employ restriction endonucleases that are sensitive to methylation of their cutting sites, so that both DNA rearrangements and DNA modifications will provide possible detectable difference sequences. Many plants have genomes that are considerably less complex than mammalian genomes and the entire genome of such plants may be represented in the "representations", A method for performing RDA, as adapted herein for plant genomes, is described below.

Representational Difference Analysis (RDA) Adapted for Plant Genomes a) General

The basic concept common to RDA and other subtractive technologies is to compare two DNAs by using one of the DNAs in excess to remove (subtract) all of the sequences held in common between the two DNA samples. Therefore, what are left are those sequences which vary between the two.

RDA depends on the use of PCR to amplify very low concentrations of DNA sequences obtained, without the need to start with prohibitively large amounts of material. The methodology is based on altering the ends of the DNA sequences so that only certain combinations can be amplified by PCR. In summary, the process depends on steadily depleting the sequences which are shared between the two DNAs being compared until only those which differ are left. The depletion is done by hybridizing using increasingly large amounts of the driver (the source of the sequences to be eliminated) with reducing amounts of the tester (the source of the sequences of interest to be isolated). After each round of hybridization, only those sequences which have formed a double stranded fragment with both strands arising from the tester (the target sequence) are amplified. This "subtraction product" is then subjected to further rounds of hybridization and amplification for enrichment of the target sequence until no further change in the subtracted fraction is expected to occur. At this point, the subtracted fraction should be sufficiently enriched that it is comprised of only (target) sequences which were initially present in the tester representation but absent from the driver representation. For plants, usually two to three rounds of hybridization and amplification are sufficient to enrich for and isolate subtracted target sequences.

Each of the subtraction fragments is then inserted into a plasmid vector for further identification and characterization.

b) Preparation of DNA

The starting material for obtaining markers of genomic polymorphism and markers of genomic integrity is DNA extracted from (i) normal plants, which are known to be genetically true-to-type, and (ii) plants which show phenotypic variation from normal (off-types). The DNA may represent entire genome of the plant cells, or may represent the nuclear genome, the mitochondrial genome, the chloroplast genome, or combinations of these. Extraction of DNA from these cellular sources is well known to those skilled in the art.

DNA may be isolated from any plant tissue including, but not limited to, leaves, stems, nodes, fruit mesocarp or pericarp, and the like. For identifying genomic polymorphisms arising in tissue culture, or the maintenance of genomic integrity therein, samples of DNA may be isolated from protoplasts, callus cells, embryos, or any other plant cells tissue culture. The DNA may be isolated by any known method including, but not limited to, extraction with a phenol/chloroform mixture, and precipitation. The DNA is digested with a restriction endonuclease either prior to or after extraction.

As described above, when preparing DNA for isolation of difference products, DNA from a single plant source is preferably digested using different restriction enzymes in separate determinations. Different restriction enzyme digests may similarly be used when preparing DNA isolated from a tissue culture source for detecting somaclonal variation. The use of a number of different restriction endonucleases that recognize different cutting site sequences to prepare amplicons is preferred, in order to reveal sequence differences that might be otherwise be masked if only a single restriction enzyme were used. In order to generate nucleic acid sequences of a size appropriate for amplification by PCR (about 2 kilobase pairs, kbp), restriction enzymes such as BamHI, BglII, HindIII that recognize a six-base nucleotide sequence are useful. Restriction enzymes that recognize a four-base sequence, such as HpaII, MspI and the like, may also be used in order to generate shorter sequences. The restriction endonucleases may provide for blunt ends or staggered ends, usually staggered ends.

The method of the invention may further employ restriction endonucleases that are sensitive to methylation of their cutting sites. Such methylation sensitive restriction enzymes are unable to cleave DNA if their cutting site is methylated, and the enzyme then proceeds to cleave at the next unmethylated cutting site. For example, to generate fragments which have DNA structural polymorphisms (e.g., point mutations, quantitative modification of repetitive DNA, excised or inserted transposable elements, and the like), restriction enzymes such as BglII, HindIII and the like, which are unaffected by the methylation status of the DNA are employed; while to isolate possible modification polymorphisms, especially methylation of DNA, then methylation sensitive restriction enzymes, such as BamHI, HpaII or the like, are employed.

For low complexity DNAs, the DNA may alternatively be prepared by shearing, or any other reproducible method of generating fragments of less than 2 kbp. This size is determined by the size of the fragments which can be reproducibly amplified by PCR. As the methodology of PCR improves, the size resolution may be increased accordingly. However, the method chosen for preparing representations will be that which will generate differences between the two plant lines being tested. Thus, it is more likely that a restriction enzyme digest would be the most appropriate method.

c) Preparation of Amplicons

Amplicons are prepared by attaching defined oligonucleotides (adaptors) at the ends of the digested DNAs and then amplifying the resultant molecules using PCR. Where DNAs are pooled, each of the amplicons is prepared separately and pooled for the hybridization reaction, described below.

The adaptors are usually staggered at both ends, with one strand being longer and serving as the sequence complementary to the PCR primer. The adaptor is double-stranded (ds) and has one end complementary to the ends of the dsDNA from the digestion. Usually, the adaptor chain complementary to the primer will be at least about 12 nucleotides (nt), more usually at least 17 nt, and generally fewer than about 200 nt, more usually fewer than about 100 nt. Any convenient method for ligation of the adaptors to the 5' ends of the tester DNA may be employed.

Adaptor sequences useful for attachment to tester DNA for generating difference products are listed in Table 1, which is reproduced in part (Bgl, Bam and Hind series) from Lisitsyn et al. (1993) and in part (Hpa series) from Ushijima et al., *Proc. Natl. Acad. Sci. USA* 94, 2284–2289 (1997). The adaptors for PCR represent nucleic acid sequences that are recognized by the appropriate restriction endonuclease and may be easily cleaved from the tester DNA at the end of each amplification step. Three or four sets of exemplary adaptors are illustrated in Table 1 for each enzyme. Thus, a different set of adaptors can be used for each of the separate stages of the RDA method, described below, one for the representation stage and the other two alternately for the hybridization/amplification stage, so that the adaptors from the representation stage do not interfere with the hybridization/amplification stage.

Once the initial amplification of representative DNA from the driver and the tester has been performed, the first set of adaptors are removed by restriction endonuclease digestion and the amplicons are purified away from the oligonucleotides by methods known to those skilled in the art, such as by chromatography using a SEPHADRX™ G25 column, by a QIAQUICK® Spin column (Qiagen, Chatsworth, Calif.), by agarose gel chromatography, or the like. The driver DNA is now in its final form.

A second set of oligonucleotide adaptors is then ligated to the tester DNA in preparation for PCR amplification of the target difference product obtained by the hybridization step. After each round of hybridization and amplification, the existing oligonucleotide adaptors are removed from the tester DNA and replaced by a different set of adaptors. No two consecutive rounds of amplification are done with the same adaptors; however, the adaptors used to generate the original amplicons may be used in a subsequent step. The change of adaptors between hybridization/amplification rounds ensures the highest possible enrichment of the target DNA subtraction product at each stage.

d) Tester and Driver Combinations for Isolating DNA Subtraction Products

Tester and driver DNA may be separately derived from normal and off-type plants from the same species (e.g., date palm), or the same cultivar, or different cultivars, in any combination. Moreover, driver or tester DNA may comprise pools of different cultivars of normal plants or pools of different off-type cultivars of the same species, in any combination. Further, the driver or tester DNA may comprise a pool of off-types of the species or of a cultivar exhibiting a variety of different phenotypic mutations (e.g., dwarfs, mosaics, and the like). Alternatively the driver DNA may comprise a pool of off-types, each exhibiting the same phenotypic mutation (e.g., dwarfism, mosaicism, and the like). Moreover, driver DNA comprising a pool of different DNAs may be used against tester DNA comprising a pool of different DNAs. The foregoing list of possible combinations is not intended to be limiting, as other useful combinations are known to those skilled in the art.

DNA subtraction products (genetic difference products) are obtained by employing normal plant DNA and off-type plant DNA as driver DNA or as tester DNA, in both directions. For example, normal plant DNA may be used as driver, and a single off-plant DNA may be used as tester. In the opposite direction, a single off-type DNA may be used as driver, and normal plant DNA used as tester. In some embodiments of the invention, pools of off-type plant DNA are preferably used as driver DNA. In other embodiments of the invention, previously isolated DNA subtraction products are added to pools of off-type or normal DNA for use as driver DNA.

The following description of embodiments of the invention employing driver DNA and tester DNA in different combinations and from differing sources is not intended to be limiting, as other combinations of driver and tester sources and combinations to obtain different types of DNA subtraction products will be apparent to those skilled in the art, from the teachings herein.

In embodiments of the invention for obtaining DNA subtraction products that are markers of genetic polymorphism in off-type plants, DNA from a normal plant is used as driver DNA, and DNA from a single off-type plant is used as tester DNA. The reverse combination, whereby normal DNA is tester and off-type DNA is driver, will also identify subtraction products which are present in the normal plant DNA, but deleted in the off-type plant DNA. By using these driver/tester combinations with many different off-type plants, a library of DNA subtraction products may be obtained as markers of genetic polymorphisms.

In another embodiment of the invention, to isolate markers of genomic integrity of plants, RDA is performed using DNA from one or more off-type plants that exhibit different mutations as driver DNA, and normal plant DNA as tester DNA. A library of DNA subtraction products may thus be obtained that represent DNA sequences present in the normal plant, and not present in the plurality of different off-type plants. Such sequences may be used as markers for regions of the normal genome that are subject to lability during tissue culture.

In another embodiment of the invention, to isolate one or more markers of genetic polymorphisms that are common to one or more, or to a plurality of different off-type plants, normal plant DNA is used as tester DNA, and a pool of DNAs from a plurality of off-type plants that exhibit different mutations is used as driver DNA. DNA subtraction products from this combination will be those which are altered in all of the off-type plants, and cannot be subtracted from the tester. These markers are those which are common to all of the off-type plants.

Another embodiment of the invention allows isolation of a marker that is specific to a particular mutation in a two stage process. Initially a set of variable sequences common to many off-types are identified by using a pooled driver DNA from a plurality of off-type plants exhibiting different mutations, and normal plant DNA as tester DNA, as in the foregoing embodiment. Then a pool of DNAs from independently arising similar off-types (e.g., dwarfs) is used as the driver DNA along with, added to this pool, the sequences already identified which are common to all the off-type plants. The tester DNA is normal plant DNA. The DNA subtraction products will be only sequences which are common to the particular off-type (i.e., dwarf), thus producing a mutation-specific marker.

e) Subtractive Hybridization/Kinetic Enrichment

Following preparation of driver and tester amplicons, the subtraction step is performed, usually in combination with a kinetic enrichment step in the same operation. (Wigler and Lisitsyn, U.S. Pat. No. 5,436,142). During these steps, the tester amplicon fragments joined to the adaptors are combined with the driver amplicon fragments and melted and allowed to reanneal. The driver amplicon fragments are present in substantial excess over the tester amplicons, usually at least a 5-fold excess, and the excess may exceed 50 or more, usually not exceeding $10^8$-fold excess, more usually not exceeding a 500-fold excess. The ratio of driver DNA to tester DNA usually is increased for successive rounds of subtraction. The increase may vary from about 1:1 to about $10^3$. Usually, the initial ratio will be in the range of about 10 to 1000-fold excess.

Usually melting will be achieved by heating at an elevated temperature, generally $\geq 95°$ C., and hybridization proceeding at about 60° C., where various buffers may be employed, as well as salt concentrations, to provide the necessary stringency. Normally, it is the presence or absence of the fragment that is being determined, so absolute stringency is not required. However, if a variant of an existing sequence is to be isolated, then increasing the stringency may allow this variant to be detected; although an increase in stringency tends to lower the rate of hybridization.

After melting and reannealing, there will be a substantial enrichment of target DNA in the total double-stranded DNA, since the target DNA will not be inhibited from self-annealing due to the lack of complementary sequences present in the driver DNA.

In carrying out the process, the first round is mainly subtractive. Subsequent rounds have a greatly increased component of kinetic enrichment, which is based on the second order kinetics of DNA reannealing, known to those skilled in the art, by which the rate of formation of double stranded DNA is higher for the DNA species of higher concentration (i.e., the more abundant a sequence is in a mixture, the more easily it can be separated from a low abundant species at low $C_o t$ values, below the $C_o t$ value for half the abundant species to reanneal). For example, if target DNA is equimolar with respect to tester DNA (i.e., a single copy), and if driver amplicon is taken in N-fold excess to tester amplicon, assuming virtually complete reannealing of driver amplicon, target will be enriched N times after the first round. After the second round, target will be enriched $N^2$ multiplied by a factor due to the subtractive component, and after the third round, at least the square of that.

f) Amplification

After melting and reannealing, overhangs are filled in by employing any convenient DNA polymerase e.g., Taq DNA polymerase, in the presence of the four deoxynucleotides (dNTP), dATP, dGTP, dCTP, dTTP, whereby only double-stranded, self-reannealed tester DNA will have filled-in adaptors at each end of the amplicon. Since the driver DNA does not inhibit target DNA from self-annealing, while the driver DNA inhibits non-target tester DNA from self-annealing, there is a substantial enrichment in the target DNA as compared to the total tester DNA.

The double-stranded self-reannealed tester amplicon is then amplified under conventional PCR conditions, usually involving at least about 5 cycles, frequently as many as 10 cycles and usually not more than about 40 cycles, preferably not more than about 30 cycles, in a multi-step procedure that includes PCR amplification, mung bean nuclease digestion, and a second PCR amplification. The purpose of the mung bean nuclease digestion is to remove single stranded DNA, which includes driver DNA, and the single-stranded products of linear amplification. Alternatively, unwanted single-stranded DNA may be removed by any other method known to those skilled in the art, including treatment with an exonuclease, such as that derived from bacteriophage lambda (i.e., λ exonuclease). The λ exonuclease degrades all driver strands having a terminal 5' phosphate group (i.e., driver strands present in a driver-driver or tester-driver duplex). Tester strands are not digested by the λ exonuclease because the tester molecules do not have 5' phosphate groups. Rather, the tester strands have the adaptors, which have 5' OH groups, ligated to their 5' ends.

g) Subsequent Rounds of Hybridization and Amplification

As described above, after the first round of hybridization and amplification, the amplified product(s) have a change of adaptors and are exposed to new driver amplicons for a second melting and reannealing. The resulting subtraction product(s) are amplified by PCR, as above. If a third round of hybridization and amplification is needed, the newly amplified product(s) are again given a new set of a adaptors and are exposed to new driver amplicons for a third melting and reannealing, followed by amplification of the final product(s) and removal of the final set of adaptors.

h) Cloning of the Subtraction Product

Bach of the final subtraction nucleic acid fragments are inserted into a plasmid vector for further identification and characterization. Cloning of the fragments are achieved by methods known to those skilled in the art, that are widely available as commercial kits. For example, if the restriction enzyme BamHI has been used to remove the final adaptors, the final subtraction fragment is cloned into the BamHI site of pBLUESCRIPT® (Stratagene, La Jolla, Calif.), according to the method recommended by the manufacturer. Similarly, if the restriction enzyme HpaII is employed, the final subtraction fragment is cloned into the HpaII of PCR-SCRIPT® (Stratagene). Other vectors for use with other enzymes are commercially available and known to those skilled in the art.

i) Characterization of Subtraction Products

Characterization of the cloned subtraction fragments includes one or more of the following:

(i) hybridization of off-type subtraction fragments to Southern blots of genomic DNA from normal plants of the same species, to determine whether or not the sequences are repetitive or are of low copy number, and whether or not they are polymorphic;

(ii) sequencing of the subtraction fragments to determine the nature of the DNA alteration which allowed the difference clone to be isolated;

(iii) designing of primers for PCR amplification of the subtraction fragments to form probes for identifying similar sequences in normal or off-type plants, in assays such as hybridization (e.g., dot blot assays, microchip DNA assays), or the like.

j) Hybridization Assay for Identification of Similar Nucleic Acid Sequences

To prepare molecular genetic probes for identification of genomic polymorphisms, the difference clones are sequenced and primer pairs developed for amplification by PCR. The probes are then used to identify similar sequences in normal DNA, off-type plant DNA, or DNA from plant cells in tissue culture. An exemplary hybridization assay is a dot blot assay. By this assay, DNA from normal or off-type plants, or from plant cells in culture, is digested with restriction endonucleases and the fragments are separated on 1% horizontal agarose gels in Tris:Borate:EDTA (TBE) buffer. The DNA is transferred to nylon membranes (NYTRAN®, Amersham/Pharmacia Biotech, Cleveland, Ohio) following denaturation in 1.5M NaCl, 0.1M NaOH and neutralization in 1.5M NaCl, 0.5M Tris.HCl, pH 6.0. The filters are hybridized and visualized using a fluorescein-labeled probe prepared according to a commercial kit (GENE IMAGES™, Amersham/Pharmacia Biotech).

k) Method for Identification of Genomic Polymorphisms Arising During Plant Cell Tissue Culture DNA is prepared from a sample of plant cells in tissue culture, as described above. A restriction endonuclease digest is prepared, and the DNA fragments are separated by electrophoresis (e.g., agarose gel electrophoresis), or other methods known to those skilled in the art that are suitable for later hybridization procedures with genetic probes prepared according to the methods of the invention.

Tissue culture DNA samples are obtained at various time intervals throughout the tissue culture process until a DNA sequence polymorphism is identified, or until the tissue culture process is completed.

TABLE 1

| Primer Pair Set | Name | Sequence | |
|---|---|---|---|
| 1 | R Bgl 24 | 5'-AGC ACT CTC CAG CCT CTC ACC GCA-3' | (SEQ ID NO:7) |
|   | R Bgl 12 | 5'-GAT CTG CGG TGA-3' | (SEQ ID NO:8) |
| 2 | J Bgl 24 | 5'-ACC GAC GTC GAC TAT CCA TGA ACA-3' | (SEQ ID NO:9) |
|   | J Bgl 12 | 5'-GAT CTG TTC ATG-3' | (SEQ ID NO:10) |
| 3 | N Bgl 24 | 5'-AGG CAA CTG TGC TAT CCG AGG GAA-3' | (SEQ ID NO:11) |
|   | N Bgl 12 | 5'-GAT CTT CCC TCG-3' | (SEQ ID NO:12) |
| 1 | R Bam 24 | 5'-AGC ACT CTC CAG CCT CTC ACC GAG-3' | (SEQ ID NO:13) |
|   | R Bam 12 | 5'-GAT CCT CGG TGA-3' | (SEQ ID NO:14) |
| 2 | J Bam 24 | 5'-ACC GAC GTC GAC TAT CCA TGA ACG-3' | (SEQ ID NO:15) |
|   | J Bam 12 | 5'-GAT CCG TTC ATG-3' | (SEQ ID NO:16) |
| 3 | N Bam 24 | 5'-AGG CAA CTG TGC TAT CCG AGG GAG-3' | (SEQ ID NO:17) |
|   | N Bam 12 | 5'-GAT CCT CCC TCG-3' | (SEQ ID NO:18) |
| 1 | R Hind 24 | 5'-AGC ACT CTC CAG CCT CTC ACC GCA-3' | (SEQ ID NO:19) |
|   | R Hind 12 | 5'-AGC TTG CGG TGA-3' | (SEQ ID NO:20) |
| 2 | J Hind 24 | 5'-ACC GAC GTC GAC TAT CCA TGA ACA-3' | (SEQ ID NO:21) |
|   | J Hind 12 | 5'-AGC TTG TTC ATG-3' | (SEQ ID NO:22) |
| 3 | N Hind 24 | 5'-AGG CAG CTG TGG TAT CGA GGG AGA-3' | (SEQ ID NO:23) |
|   | N Hind 12 | 5'-AGC TTC TCC CTC-3' | (SEQ ID NO:24) |
| 1 | R Hpa 24 | 5'-AGC ACT CTC CAG CCT CTC ACC GAC-3' | (SEQ ID NO:25) |
|   | R Hpa 11 | 5'-CGG TCG GTG AG-3' | (SEQ ID NO:26) |

TABLE 1-continued

| Primer Pair Set | Name | Sequence | |
|---|---|---|---|
| 2 | J Hpa 24 | 5'-ACC GAC GTC GAC TAT CCA TGA AAC-3' | (SEQ ID NO:27) |
|   | J Hpa 11 | 5'-CGG TTT CAT GG-3' | (SEQ ID NO:28) |
| 3 | N Hpa 24 | 5'-AGG CAA CTG TGC TAT CCG AGG GAC-3' | (SEQ ID NO:29) |
|   | N Hpa 11 | 5'-CGG TCC CTC GG-3' | (SEQ ID NO:30) |
| 4 | S Hpa 24 | 5'-ACT TCT ACG GCT GAA TTC CGA CAC-3' | (SEQ ID NO:31) |
|   | S Hpa 12 | 5'-CGG TGT CGG AAT-3' | (SEQ ID NO:32) |

EXAMPLES

Example 1
General RDA Method to Obtain Nucleic Acid Sequence Difference Products from Plants Genomes An general method for RDA to obtain nucleic acid sequence difference products in plants is described below. This method was adapted from a Laboratory Manual supplied by Lisitsyn and Wigler of Cold Spring Harbor Laboratories for RDA using mammalian genomes [See also, Lisitsyn et al. (1993)].

a) Isolation of DNA

One to 2 grams of leaf material from a plant were ground in liquid nitrogen to a fine powder. The powder was added to 10 ml of preheated extraction buffer [2% w/v hexadecyltrimethyl ammonium bromide (CTAB), 100 mM Tris.HCl, pH 8.0, 1.4M NaCl, 20 mM EDTA, 0.1% mercaptoethanol] and incubated at 65° C. for 30 minutes with occasional shaking. Fifteen ml of chloroform:isoamyl alcohol (24:1) were added and shaken for 15 minutes. The mixture was centrifuged at 5,000×g for 5 minutes and the aqueous phase collected. The DNA was precipitated by the addition of an equal volume of ice cold isopropanol and collected on a sealed Pasteur pipette. The DNA was redissolved in 200 µl of TE buffer (10 mM Tris.HCl, 1 mM EDTA, pH 8.0).

b) Preparation of Amplicons

Two micrograms of DNA from each of the plants to be used as tester or driver were digested with 80 units of an appropriate restriction enzyme (HindIII, BamHI, BglII, or the like) in a final reaction mixture of 200 µl. The digests had 100 µg of yeast tRNA added and were extracted with 200 µl of phenol/chloroform (equal volumes of phenol and chloroform). The upper phase was removed and 18 µl of 3M sodium acetate added, followed by the addition of 600 µl of 100% ethanol to precipitate DNA. After mixing, the solution was placed at −70° C. for 10 minutes, at 37° C. for 2 minutes and the precipitate collected by centrifugation in a microcentrifuge at full speed for 10 minutes. The precipitate was washed in 70% ethanol and dried. The digested DNAs were dissolved in 18 µl of TE buffer, pH 8 (nominally at a concentration of 100 µg/ml). The concentration was checked by running a sample of each digest on an agarose gel with known amounts of sheared herring sperm DNA as standards, as described below.

c) Ligation of Adaptor Sequences

One µg digested DNA, 7.5 µl of the appropriate primer set, depending on which enzyme was used initially (e.g., R HindIII 12 and 24, or R BamHI 12 and 24 or R Bgl 12 and 24), 3 µl of 10×ligase buffer and water to 30 µl were mixed in a microcentrifuge tube. The tubes were placed in a heating block at 55° C. and the block was then placed at 4° C. for 60 to 75 minutes (until the temperature had fallen to 12° C.). The tubes were then placed on ice for 3 minutes, then 1 µl of T4 ligase was added and the cooled mixture was incubated at 16° C. overnight. The ligation reaction was diluted with 970 µl of TE buffer, pH 8, and the amplification reactions set up in a microcentrifuge tube, as follows:

80 µl 10×ExTaq buffer
64 µl dNTP mix
16 µl of one primer of the appropriate pair (e.g.,R Hind 24 or R Bam 24)
80 µl of the diluted ligation mixture
560 µl water The tube was placed in a heating block at 720° C. for 5 minutes (this melts off the 12 mer oligonucleotide). Six µl of Taq polymerase was added and mixed by pipetting. The mixture was then aliquoted into 8 PCR tubes in a Perkin-Elmer thermocycler, the block of which was being held at 72° C. After 5 minutes, the thermocycler program run was:

20 cycles: 95° C. for 11 seconds; 72° C. for 2 minutes, 7 seconds, followed by 10 minute at 72° C., followed by holding at 4° C.

The 8 tubes were combined and a 10 µl aliquot was run on a 1.5% agarose/TBE gel at 100 V for 30 minutes to check the amplification. Driver and tester amplicons were run in adjacent lanes to check that similar patterns were obtained. The remainder was extracted with 600 µl of phenol/chloroform. Seven hundred fifty µl of the upper phase was removed and 75 µl of 3M sodium acetate added, followed by 825 µl of propanol. The tube was mixed by inversion and left on ice for 15 minutes. The precipitate was collected by centrifugation for 15 minutes at full speed in a microcentrifuge, washed twice with 70% ethanol and dried. The amplicons were redissolved in 80 µl of TE buffer (assuming that 40 µg of DNA were produced in each 800 µl PCR reaction). The DNA which was to be used as driver was amplified in 8 reactions (6.4 ml total of PCR reaction mixture), while the tester DNAs were amplified in a single reaction. The concentrations of both tester and driver amplicons were estimated by electrophoresis on a 1.5% agarose/TBE gel with sheared herring sperm DNA standards.

d) Removal of Adaptors From Amplicons

One hundred fifty µg of the driver and 10 µg of the tester amplicons were digested with the appropriate enzyme in 800 µl and 200 µl, respectively, at an enzyme concentration of 20 units/µg DNA, at 37° C. for one hour. Yeast tRNA (10 µg) was added and each digest extracted with phenol/chloroform. The DNA was precipitated with an equal volume of isopropanol following the addition of ⅒th volume of 3M sodium acetate, as described above. The driver and tester DNAs were both redissolved at approximately 400 µg/ml. Both the digested driver and tester amplicons were run on a 1.5% gel alongside an equal aliquot of undigested amplicons to check the completeness of the digestion. On the same gel, standard herring sperm DNA was run so that the final concentrations of driver and tester DNAs were estimated. Both the driver DNA and tester DNA were adjusted to 400 µg/ml.

e) Change of Adaptors on Tester Amplicon.

Two μl of the tester amplicons were loaded into a 0.5 cm well in a 1.5% agarose gel in Tris/acetate buffet, with the loading dye containing xylene cyanol, bromophenol blue and orange G. The gel was run so that the bromophenol blue migrated about 1 cm. The gel slice from the top of the xylene cyanol band to the mid-point between the bromophenol blue and the orange G was excised (this contains fragments having a size of from about 2 kbp to about 150 bp). The DNA in the gel fragment was extracted using the QIAGEN® gel extraction kit and the concentration checked by gel electrophoresis. One μg of the extracted DNA was ligated to a second set of oligonucleotide adaptors exactly as described for the preparation of the original amplicons. The ligation reaction was then diluted to a final volume of 100 μl with water. Following the ligation reaction, an aliquot of the ligate was amplified for 20 cycles in a reaction volume of 20 μl to check that the newly ligated adaptors would support amplification with the new primer.

f) Subtractive Hybridization/Kinetic Enrichment

The hybridization reaction was set up by mixing 80 μl of driver (500 μg/ml) with 40 μl (100 μg/ml) (a ratio of driver:tester of 100:1). To this was added 30 μl of 10M ammonium acetate, mixed by pipetting, followed by the addition of 380 μl of ethanol. The mixture was incubated at −70° C. for 10 minutes, at 37° C for 2 minutes, and the precipitate collected by centrifugation for 10 minutes at full speed in a microcentrifuge. The pellet was washed twice with 70% ethanol and vacuum dried. The pellet was redissolved in 4 μl of 3×EE buffer [30 mM N-(2-hydroxyethyl piperizine)-N'-(3-propene sulfonic acid) (EPPS), pH 8.0, 3 mM EDTA] followed by repeated vortexing interspersed with centrifugation. The solution was collected at the bottom of the tube and overlaid with light mineral oil so that the spherical droplet could be seen to be completely covered by oil. The DNA was denatured by replacing in a heating block at 98° C. for 5 minutes. One μl of 5M sodium chloride solution was added and the tube briefly centrifuged to mix the aqueous phases. The DNA was incubated at 67° C. overnight. The oil was removed by carefully pipetting and 390 μl of TE buffer, pH 8, and 40 μg tRNA were added to the DNA. The appropriately annealed fragments were amplified in the following reaction:

80 μl 10×ExTaq buffer

64 μl dNTP mix

80 μl of the diluted ligation mixture

560 μl water

6 μl of Taq polymerase

The tube was placed in a heating block at 72° C. for 5 minutes to fill in the ends. Sixteen μl of the appropriate primer (the 24 mer used in the adapter) was added, mixed by pipetting, and the mixture aliquoted into 8 PCR tubes in a Perkin-Elmer thermocycler, the block of which was being held at 72° C.

The thermocycler program run was 10 cycles of 95° C. for 11 seconds; 72° C. for 2 minutes, 7 seconds, followed by 10 minutes at 72° C., followed by holding at 4° C.

The tubes were combined and 20 μl subjected to a further 20 cycles of amplification under the same conditions.

Ten μg of tRNA was added to the remainder of the amplified reaction and then extracted with 600 μl phenol/chloroform. Seven hundred fifty μl was removed, 75 μl of 3M sodium acetate added, followed by 825 μl propanol. After incubation on ice for 15 minutes, the precipitate was collected by centrifugation, washed twice with 70% ethanol and dissolved in 40 μl of TE buffer, pH 8. At this stage, the aliquot subjected to additional amplification cycles was run on a 1.5% agarose gel to check that amplification has occurred. Twenty μl of this first round difference product was digested with 20 units of mung bean nuclease at 30° C. for 30 minutes. The reaction was stopped by the addition of 160 μl of TE buffer, pH 8. The digested product was amplified in a reaction mixture consisting of:

80 μl 10×ExTaq buffer

64 μl dNTP mix

16 μl of the same primer used for the 10 cycle amplification

80 μl of the diluted ligation mixture

560 μl water

6 μl of Taq polymerase

The mixture was aliquoted into 8 PCR tubes in a Perkin-Elmer thermocycler, the block of which was being held at 72° C.

The thermocycler program run was 20 cycles: 95° C. for 11 seconds; 72° C. for 2 minutes, 7 seconds, followed by 10 minutes at 72° C., followed by holding at 4° C.

The 8 tubes were combined and a 10 μl aliquot was run on a 1.5% agarose/TBE gel at 100 V for 30 minutes to check the amplification. The remainder was extracted with 600 μl of phenol/chloroform. Seven hundred fifty μl of the upper phase was removed and 75 μl of 3M sodium acetate added, followed by 825 μl of propanol. The tube was mixed by inversion and left on ice for 15 minutes. The precipitate was collected by centrifugation for 15 minutes at full speed in a microcentrifuge, washed twice with 70% ethanol and dried. The amplicons were redissolved in 80 μl of TE buffer, pH 8. The concentration was estimated by electrophoresis on a 1.5% agarose/TBE gel with sheared herring sperm DNA standards and adjusted to 100 μg/ml.

Five μg of this difference product was digested with 100 units of enzyme in 100 μl at 37° C. for 30 minutes. Ten μg of tRNA was added and the difference product extracted with phenol/chloroform and recovered by ethanol precipitation. The pellet was dissolved in 100 μl of TE buffer, pH 8, and the concentration adjusted to 20 μg/ml. Five μl (100 nag) of this product was ligated to the third set of adapters in 30 μl, as described previously. The ligate was diluted with 50 μl of TE buffer, pH 8, containing tRNA (20 μg/ml).

g) Second Round Hybridization/Amplification

The second hybridization was set up with 40 μl of the difference product (50 nag), 80 μl (40 μg) of the driver and the hybridization carried out exactly as described previously.

The second round difference product was subjected to 25 rounds of amplification after the mung bean nuclease digestion, in order to generate sufficient product.

h) Third Round Hybridization/Amplification

The adaptors were changed again to reuse the same set as that used for the first hybridization/kinetic enrichment step. In this step, 400 pg of the difference product with changed adaptors was mixed with 40 μg of driver and the hybridization steps followed again. This difference product was again subject to 25 cycles of amplification after the mung bean nuclease digestion.

i) Cloning of Difference Products

A comparison (side by side gel electrophoresis) of the second and third round subtractions indicates whether or not an additional round of subtraction is necessary. If not, then 2 μg of the final subtraction product was digested with 50 units of enzyme. One hundred ng of the digest was mixed with 100 ng of pUC18 vector digested with the same enzyme (a ratio of about 10:1 target to vector ends), extracted with phenol/chloroform and precipitated with ethanol. The precipitate was washed twice with 70% ethanol and redissolved in 8 μg water. To this was added 1 μl 10×ligase buffer and 1 μl T4 ligase, and the mixture incubated overnight at 16° C. Two μl of the ligate was used to transform supercompetent JM109 cells and the recombinant colonies picked. The initial characterization of the recombinants can be made by colony hybridization to place the clones into groups based on their repetitiveness in the final difference product.

Example 2
Isolation and Characterization of Difference Clones From Banana Plants This Example illustrates that difference clones can be isolated from a subtraction between a tissue culture-induced off-type banana plant and a normal plant of the same cultivar. The restriction enzyme HpaII was employed to prepare the restriction digests and generate the subtraction difference product library. This restriction enzyme is sensitive to inhibition of its cutting site (e.g., by methylation), and both DNA rearrangements and DNA modifications are possible isolatable difference sequences.

To isolate difference clones, the general RDA method to obtain nucleic acid sequence difference products from plant genomes, described in Example 1, was employed, with the following exceptions: to prepare amplicons, the endonuclease digestion was performed in a total volume of 100 μl instead of 200 μl; DNA extraction was performed with phenol:chloroform:isoamyl alcohol (in equal volumes); and 100 μg of tRNA was added as a carrier, instead of 10 μg. Ligation of adaptors was performed in a volume of 50 μl, instead of 25 μl; the PCR reaction when generating the driver amplicons was run for 25 cycles, instead of 20 cycles; the first difference product was amplified for 28 cycles, instead of 20 cycles; and the second subtraction products were amplified for 27 cycles, instead of 20 cycles.

In this Example, two μg of DNA from the leaves of two plants, the cultivar "Williams" and an off-type arising from tissue culture, which was classified as exhibiting two frequently observed aberrations, masada and chlorotic (labeled "#3" and referred to as such subsequently). Restriction digests were prepared from the two DNAs with HpaII at 100 units/μg. After one hour of digestion at 37° C., an additional 100 units of enzyme were added and the incubation continued for a further one hour. The extent of digestion of the two samples was then checked by agarose gel electrophoresis.

The adaptors Hpa 1 and 2 (see Table 1) were ligated to Williams DNA and #3 DNA, respectively, and the resulting ligates were amplified by PCR to produce the first round amplicons. Aliquots of each of the Williams and #3 amplicons were again digested and the digestion checked by agarose gel electrophoresis.

Two different subtraction procedures were performed, one with Williams DNA as the tester and #3 as the driver, and the other with #3 DNA as the driver and Williams DNA as the tester.

A second set of adaptors was added to the respective tester DNA, and the first round subtractions carried out. Following amplification of the difference products, two additional rounds of subtraction were performed to generate the final difference products.

The difference products were cloned into the vector PCRSCRIPT® (Stratagene). The resulting clones were screened by hybridization with fluorescein-labeled amplicons from both Williams and #3 to confirm that they were difference clones. Clones that gave the most clear-cut hybridization results were selected for further characterization.

Subtraction Products

When Williams was used as the tester and #3 was used as the driver, no difference products were obtained after the first, second or third round subtraction. This result shows that all the fragments present in the Williams HpaII-produced amplicons are also in the off-type HpaII-produced amplicons.

However, when #3 was used as the tester and Williams was used as the driver, difference products were obtained. Following three rounds of subtraction, the difference products were cloned and two of these (Hpa-5 and Hpa-15) were characterized further.

Partial sequences of Hpa-5 and Hpa-15 are given below (n=unidentified nucleotide). Primer pairs for PCR were developed from the partial sequences. The location of the sequences from which the primer pairs were developed are underlined. The left primer developed from Hpa-5 begins with "tcg", the right primer is the inverse of the sequence from right to left beginning "gag". The left primer developed from Hpa-15 begins with "tgg", the right primer is the inverse of the sequence from right to left beginning "aca".

Partial Sequence of HPA-5

```
aggcaactgt gctatccgag ggaccgggat        (SEQ ID NO:1)
ggcgctctgg cgaacatcgt acggcggcgg
aggagtgtca cagctgcgac ggcggcggcg
agcgatccat ggcctcggct cgattcggtc
caaaaagatg gcgctttgtt gttcttttga
cactgacgag ggagtgtgag ctgacgccgg
tccctcggat agcacagttg cctgggctag
agcggc
```
HPA-5 Primer Pairs Used for PCR

```
(Left)   tcgattcggt ccaaaaagat          (SEQ ID NO:2)
(Right)  ctctagccca ggcaactgtg          (SEQ ID NO:3)
```
Partial Sequence of HPA-15

```
aggcaactgt gctatccgag ggaccggcag        (SEQ ID NO:4)
cacaccatgc nctgccacca atccatncnn
tnntggccct gaaagtagga atgacgagga
ggaggaggtt aagaacggnc nngcaggaag
tagatacaga gagagctaan nnnnagggga
gancacctac cctcgtagtg naganacacg
ttgcctcgtg cnnngtcatc acacagtccn
attcctctcc atcgtctcca tctttatcca
gcctcctgcc tctcttgtca cattaccgca
tcttttgtcc tcctcngcgg gatgtgttgt
tccattcatc tctcgtccgg tccctcggat
agcacagttg cct
```
HPA-15 Primer Pairs Used for PCR

```
(Left)   tggccctgaa agtaggaatg          (SEQ ID NO:5)
(Right)  tgtgacaaga gaggcaggag          (SEQ ID NO:6)
```

Example 3
Ability of Subtraction Products to Identify and Distinguish Between Different Banana Genotypes To determine whether the banana difference products Hpa-5 and Hpa-15 isolated from cultivar #3 could distinguish between different banana genotypes and off-types, DNA digests from the leaves of a number of different cultivars and mutants were prepared. In particular, the selected cultivars were Williams, Grand Nain (developed from a mutant Williams), dwarf Grand Nain, FHIA1, FIHA21, FIHA3, and Yangambi. The FIHA series was a breeding selection from the FHIA research station in Honduras.

The primer pairs from the subtraction products, Hpa-5 and Hpa-15, isolated in Example 2, were used for PCR amplification of the appropriate sequences in the test lines. The results of the amplifications are shown in FIGS. 1–4.

FIGS. 1 and 2 illustrate side by side agarose gel electrophoreses of PCR amplifications of DNAs from various banana cultivars, using the primer pair developed from the genetic probe Hpa-15. The first lane in each Figure is a molecular weight marker. The remaining lanes are as follows: (-), no DNA control; lanes 1-4, independent extraction of Williams leaves; lanes 5-10, various samples of other normal cultivars FIHA1 (lanes 5 and 6), FIHA 21 (lanes 7 and 9), FIHA 3 (lane 8) and Yangambi (lane 10); Grand Nain cultivars (lanes 11, 12 and 13); dwarf Grand Nain off-types (lanes 14 and 15); lanes 17-22, previously identified off-types of the Williams cultivar (lanes 17-22).

It is clear that the Hpa-15 probe is capable of distinguishing between different banana genotypes. No distinct bands are observable with Williams, confirming that the Hpa-15 probe represents a genetic difference from Williams. However, distinct hybridization bands are observable with FHIA 3 and Yangambi, lanes 8 and 10, respectively, which are phenotypically normal banana plants obtained through tissue culture. These two plant lines thus demonstrate a genetic polymorphisms detectable by the Hpa-15 probe. Distinct bands are also seen in lanes 11-15, Grand Nain and dwarfNain. This is not surprising, as Grand Nain was developed from a mutant Williams. Thus, Grand Nain demonstrates a genetic polymorphism detectable by the Hpa-15 probe. FIG. 2 illustrates that the Hpa-15 probe was capable of distinguishing each of the off-types in lanes 17, 19 and 22. However, Hpa-15 was not suitable for distinguishing between normal Grand Nain and dwarf Grand Nain, indicating that Hpa-15 is not a marker for "dwarf", but is a more general marker for off-types.

FIGS. 3 and 4 illustrate the same DNAs as in FIGS. 1 and 2, amplified with a primer pair developed from the genetic probe, Hpa-5, generated as a DNA difference product by RDA between the normal banana cultivar, Williams, and the off-type cultivar, #3. The lanes are in the same order as those described for FIGS. 1 and 2. The Hpa-5 probe was similarly capable of distinguishing between the banana genotypes. As illustrated in FIGS. 3 and 4, no distinct bands are observable with three of the Williams normal plants, confirming that the Hpa-5 probe represents a genetic difference from these three Williams. However, there is a possible band in lane 2, indicating that this Williams plant which is phenotypically normal, may have a genetic polymorphism detectable by Hpa-5. There are also possible bands in lanes 6, 7, 8 and 10 (FIHA1, FIHA 21, FIHA3 and Yangambi) which are phenotypically normal banana plants obtained through tissue culture. Bands are also observable in lanes 12 and 13 (Grand Nain and lane 14 (dwarf Grand Nain). The Hpa-5 probe was also capable of distinguishing each of the off-types in lanes 17 through 22.

FIG. 5 illustrates a repeat amplification of the off-type DNAs in lanes 17-22 of FIGS. 1-4, using the primer pair developed from the Hpa-5 probe (lanes 1-6) and the Hpa-15 probe (lanes 7-12). Lane "C" is the no DNA control. As illustrated, each of the probes identify a different polymorphism in the off-types.

Example 4

Isolation of Difference Clones Using a Pool of Mutant Flax Plants as Driver Against a Normal Tester This Example illustrates that DNA subtraction products were obtained using a mixture of DNAs from multiple lines of mutant plants as driver DNA against a single normal tester DNA.

The inbred flax variety Stormont Cirrus was employed in this example. The normal Stormont Cirrus line is termed Plastic (P1). Independently arising off-type lines employed in this example were $L_6$, $S_6$, $C_2$, and $L_H$. The restriction enzyme BamHI was employed to prepare the restriction digests and generate the subtraction difference product library. To isolate difference clones, the RDA method described in Example 1 was employed.

Figure 6:
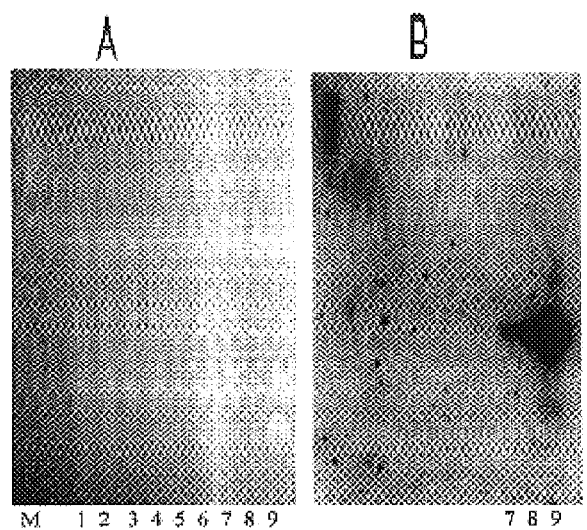
FIGS. 6A and 6B illustrate the results of RDA using a BamHI digest of DNA from normal (P1) plants of the inbred flax variety Stormont Cirrus as tester DNA against a pool of DNA from multiple off-type Stormont Cirrus lines as driver DNA.

P1 DNA was used as the tester DNA, against each of the four off-type DNAs as driver DNA, and against a mixture of the DNA amplicons from the four off-type cell lines as driver DNA. FIG. 6A shows the amplicons from P1 and the four off-types, as well as the combined amplicons and the products from three rounds of subtraction. In FIG. 6A, the lanes represent the following: M, the molecular weight marker VI (Boehringer Manheim); amplicons of P1 (1), $L_6$ (2), $S_6$ (3), $C_2$ (4) and $L_H$ (5), a mixture of 2, 3, 4 and 5 (6); first (7), second (8) and third (9) round subtractions of P1 (tester) and the mixture (6) (driver). The gel was visualized by ethidium bromide (Amersham/Pharmacia Biotech).

DNA subtraction products are clearly seen by the third round subtraction in lane 9. One of these products was isolated and cloned, and designated "4-2".

The gel of FIG. 6A was transferred by blotting to a nitrocellulose filter and hybridized with a fluorescein-labeled cloned probe 4-2. FIG. 6B illustrates that clone 4-2 is present as a first, second and third subtraction product in lanes 7, 8, and 9.

Figure 7:
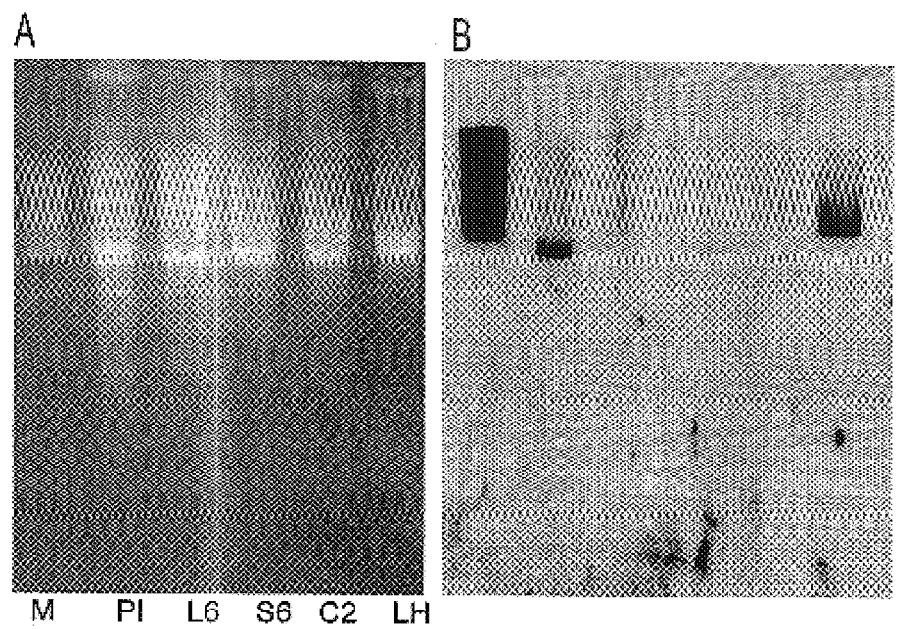
FIGS. 7A and 7B illustrate agarose gel electrophoresis and Southern blot, respectively, of BamHI digested genomic DNAs from P1 and each of the four off-types, and hybridized with clone 4-2.

FIGS. 7A and 7B illustrate agarose gel electrophoresis and Southern blot of BamHI digested genomic DNAs from P1 and each of the four off-types, and hybridized with clone 4-2. A genomic clone containing homology to 4-2 is seen in the $L_H$ lane in FIG. 7B.

While the invention has been described herein with reference to the preferred embodiments, it is to be understood that it is not intended to limit the invention to the specific forms disclosed. On the contrary, it is intended to cover all of the manifold modifications and alternative forms falling within the spirit and scope of the invention.

We claim:

1. A method for detecting genomic destabilization in a phenotypically normal plant regenerated from tissue-cultured plant cells, said genomic destabilization arising during tissue culture of the plant cells, the method comprising the steps of:
   (a) providing a plurality of DNA subtraction products obtained by:
      (1) isolating DNA from (i) a normal plant, and (ii) a plurality of off-type plants of the same species as the normal plant, wherein each of the off-type plants has a different phenotypic mutation; and
      (2) performing representational difference analysis to obtain a plurality of DNA subtraction products corresponding to a plurality of genetic sequence differences between the DNA of the off-type plants and the DNA of the normal plant, wherein the genetic sequence differences include silent mutations that are not phenotypically expressed in the off-type plants;
   (b) isolating DNA from a sample of plant cells prior to tissue culture, wherein the plant cells are of the same species as the plants in step (a)(1);
   (c) using the plurality of DNA subtraction products as genetic probes to detect existing genetic polymorphisms in the DNA from the sample of plant cells;
   (d) growing the plant cells in tissue culture;
   (e) regenerating a phenotypically normal plant from the plant cells in tissue culture thereby producing a phenotypically normal regenerated plant;
   (f) isolating DNA from the phenotypically normal regenerated plant; and
   (g) using the plurality of DNA subtraction products as genetic probes to detect a new genetic polymorphism in the DNA of the phenotypically normal regenerated plant, wherein the new genetic polymorphism was not among the existing genetic polymorphisms detected in step (c) and has arisen during tissue culture of the plant cells, thereby detecting genomic destabilization in a phenotypically normal plain regenerated from tissue-cultured plant cells.

2. The method of claim 1, wherein step (a)(2) includes amplifying at least one of the plurality of DNA subtraction products to obtain a genetic probe comprising a nucleic acid sequence corresponding to at least one of the plurality of genetic sequence differences.

3. The method of claim 1, wherein step (a)(2) includes substep of characterizing at least one of the plurality of DNA subtraction products, wherein the characterizing includes designing primers suitable for PCR amplification of at least one of the plurality of genetic sequence differences.

4. The method of claim 3, wherein steps (c) and (g) include using the designed primers in PCR amplification to detect existing genetic polymorphisms of (c) and the new genetic polymorphism of (g).

5. The method of claim 1, wherein isolating DNA from the normal plant in step (a)(1) comprises isolating DNA from a plurality of normal plants.

6. The method of claim 1, wherein the representational difference analysis in step (a)(2) comprises using DNA of the normal plant as driver DNA and DNA of the off-type plants as tester DNA, and wherein at least one of the plurality of DNA subtraction products is a marker of genetic mutation in the off-type plants.

7. The method of claim 1, wherein the representational difference analysis in step (a)(2) comprises using DNA of the off-type plants as driver DNA and DNA of the normal plant as tester DNA, and wherein at least one of the plurality of DNA subtraction products is a marker of a normal nucleic acid sequence that is not present in the DNA of the off-type plants.

8. The method of claim 1, wherein the new genetic polymorphism detected in the DNA of the phenotypically normal regenerated plant comprises a genetic sequence difference between the DNA of the normal plant and the DNA of the off-type plants that is common to DNAs from off-type plants having different phenotypic mutations.

9. The method of claim 1, wherein the normal and plurality of off-type plants of step (a)(1) are selected from the group consisting of vegetable crops, cereal crops, grasses, ornamental plants, trees, and transgenic plants.

10. The method of claim 1, wherein the normal and plurality of off-type plants of step (a)(1) are selected from the group consisting of bananas, oil palms, date palms, pineapples, plantain, papaya, flax, sugar cane, rhododendron, eucalyptus and coffee.

11. The method of claim 1, wherein the isolating steps (b) and (f) comprise isolating DNA from a source selected from the group consisting of the nucleus, the mitochondria, the chloroplasts, and combinations thereof.

12. A method for detecting genomic destabilization in a phenotypically normal plant regenerated from tissue-cultured plant cells, said genomic destabilization arising during tissue culture of the plant cells, the method comprising the steps of:

(a) providing DNA subtraction products obtained by:
  (1) isolating DNA from (i) a plurality of normal plants of a single species, and (ii) an off-type plant of the same species as the normal plants; and
  (2) performing representational difference analysis to obtain a plurality of DNA subtraction products corresponding to genetic sequence differences between DNAs of the normal plants and between the DNA of the normal plants and the DNA of the off-type plant, wherein the genetic sequence differences include silent mutations that are not phenotypically expressed in the off-type plant;
(b) isolating DNA from a sample of plant cells prior to tissue culture, wherein the plant cells are of the same species as the plants in step (a)(1);
(c) using the plurality of DNA subtraction products as genetic probes to detect existing genetic polymorphisms in the DNA from the sample of plant cells;
(d) growing the plan: cells in tissue culture;
(e) regenerating a phenotypically normal plant from die plain cells in tissue culture thereby producing a phenotypically normal regenerated plant;
(f) isolating DNA from the phenotypically normal regenerated plant; and
(g) using the plurality of DNA subtraction products as genetic probes to detect a new genetic polymorphism in the DNA of the phenotypically normal regenerated plant, wherein the new genetic polymorphism was not among the existing genetic polymorphisms detected in step (c) and has arisen during tissue culture of the plant cells, thereby detecting genomic destabilization in a phenotypically normal plant regenerated from tissue-cultured plant cells.

13. The method of claim 12, wherein step (a)(2) includes amplifying at least one of the plurality of DNA subtraction products to obtain a genetic probe comprising a nucleic acid sequence corresponding to at least one of the genetic sequence differences.

14. The method of claim 12, wherein step (a)(2) includes the a substep of characterizing at least one of the plurality of DNA subtraction products, wherein the characterizing includes designing primers suitable for PCR amplification of at least one of the genetic sequence differences.

15. The method of claim 14, wherein steps (c) and (g) include using the designed primers in PCR amplification to detect existing genetic polymorphisms of (c) and the new genetic polymorphism of (g).

16. The method of claim 12, wherein isolating DNA from the off-type plant in step (a)(1) comprises isolating DNA from a plurality of off-type plants.

17. The method of claim 12 wherein the representational difference analysis in step (a)(2) comprises using DNA of the normal plants as driver DNA and DNA of the off-type plant as tester DNA, and wherein at least one of the plurality of DNA subtraction products is a marker of genetic mutation in the off-type plant.

18. The method of claim 12, wherein the representational difference analysis in step (a)(2) comprises using DNA of the off-type plant as driver DNA and DNA of the normal plants as tester DNA, and wherein at least one of the plurality of DNA subtraction products is a marker of a normal nucleic acid sequence that is not present in the DNA of the off-type plant.

19. The method of claim 12, wherein the new genetic polymorphism detected in the DNA of the phenotypically normal regenerated plant comprises a genetic difference between the DNA of the normal plants and the DNA of the off-type plant that is common to DNAs from off-type plants having different phenotypic mutations.

20. The method of claim 12, wherein the off-type and plurality of normal plants of step (a)(1) are selected from the group consisting of vegetable crops, cereal crops, grasses, ornamental plants, trees, and transgenic plants.

21. The method of claim 12, wherein the off-type and plurality of normal plants of step (a)(1) plants are selected from the group consisting of bananas, oil palms, date palms, pineapples, plantain, papaya, flax, sugar cane, rhododendron, eucalyptus and coffee.

22. The method of claim 12, wherein the isolating steps (b) and (f) comprise isolating DNA from a source selected from the group consisting of the nucleus, the mitochondria, the chloroplasts, and combinations thereof.

* * * * *

UNITED STATES PATENT AND TRADEMARK OFFICE
CERTIFICATE OF CORRECTION

PATENT NO. : 6,773,889 B2
DATED : August 10, 2004
INVENTOR(S) : Christopher A. Cullis, Samantha Rademan and Karl Kunert It is certified that error appears in the above-identified patent and that said Letters Patent is hereby corrected as shown below:

Column 35,
Line 59, change "plain" to -- plant --
Line 67, insert -- a -- before "substep"

Column 37,
Line 1, after "providing" insert -- a plurality of --
Line 19, change "plan:" to -- plant --
Line 20, change "die" to -- the --
Line 21, change "plain" to -- plant --
Line 41, delete "the" before "a substep"

Column 38,
Line 24, after "genetic" insert -- sequence --
Line 33, after "step (a)(1)" delete "plants"

Signed and Sealed this

Seventh Day of December, 2004

JON W. DUDAS
*Director of the United States Patent and Trademark Office*

SEQUENCE LISTING

<160> NUMBER OF SEQ ID NOS: 32

<210> SEQ ID NO 1
<211> LENGTH: 216
<212> TYPE: DNA
<213> ORGANISM: Musa/paradisiaca
<220> FEATURE:
<221> NAME/KEY:
<222> LOCATION:

```
<223> OTHER INFORMATION:
<300> PUBLICATION INFORMATION:

<400> SEQUENCE: 1
aggcaactgt gctatccgag ggaccgggat ggcgctctgg cgaacatcgt            50
acggcggcgg aggagtgtca cagctgcgac ggcggcggcg agcgatccat           100
ggcctcggct cgattcggtc caaaaagatg gcgctttgtt gttcttttga           150
cactgacgag ggagtgtgag ctgacgccgg tccctcggat agcacagttg           200
cctgggctag agcggc                                                216

<210> SEQ ID NO 2
<211> LENGTH: 20
<212> TYPE: DNA
<213> ORGANISM: Musa/paradisiaca
<220> FEATURE:
<221> NAME/KEY:
<222> LOCATION:
<223> OTHER INFORMATION:
<300> PUBLICATION INFORMATION:

<400> SEQUENCE: 2
tcgattcggt ccaaaaagat                                             20

<210> SEQ ID NO 3
<211> LENGTH: 20
<212> TYPE: DNA
<213> ORGANISM: Musa/paradisiaca
<220> FEATURE:
<221> NAME/KEY:
<222> LOCATION:
<223> OTHER INFORMATION:
<300> PUBLICATION INFORMATION:

<400> SEQUENCE: 3
ctctagccca ggcaactgtg                                             20

<210> SEQ ID NO 4
<211> LENGTH: 343
<212> TYPE: DNA
<213> ORGANISM: Musa/paradisiaca
<220> FEATURE:
<221> NAME/KEY:
<222> LOCATION:
<223> OTHER INFORMATION: n means not determined; synthetic cloned
      subtraction product from PCR amplification.
<300> PUBLICATION INFORMATION:

<400> SEQUENCE: 4
aggcaactgt gctatccgag ggaccggcag cacaccatgc nctgccacca            50
atccatncnn tnntggccct gaaagtagga atgacgagga ggaggaggtt           100
aagaacggnc nngcaggaag tagatacaga gagagctaan nnnnaggga           150 gancacctac cctcgtagtg naganacacg ttgcctcgtg cnnngtcatc           200
acacagtccn attcctctcc atcgtctcca tctttatcca gcctcctgcc           250
tctcttgtca cattaccgca tcttttgtcc tcctcngcgg gatgtgttgt           300
tccattcatc tctcgtccgg tccctcggat agcacagttg cct                  343

<210> SEQ ID NO 5
<211> LENGTH: 20
<212> TYPE: DNA
<213> ORGANISM: Musa/paradisiaca
<220> FEATURE:
```

```
<221> NAME/KEY:
<222> LOCATION:
<223> OTHER INFORMATION:
<300> PUBLICATION INFORMATION:

<400> SEQUENCE: 5
tggccctgaa agtaggaatg                                              20

<210> SEQ ID NO 6
<211> LENGTH: 20
<212> TYPE: DNA
<213> ORGANISM: Musa/paradisiaca
<220> FEATURE:
<221> NAME/KEY:
<222> LOCATION:
<223> OTHER INFORMATION:
<300> PUBLICATION INFORMATION:

<400> SEQUENCE: 6 caaga gaggcaggag                                                   20

<210> SEQ ID NO 7
<211> LENGTH: 24
<212> TYPE: DNA
<213> ORGANISM: Bacillus globigii
<220> FEATURE:
<221> NAME/KEY:
<222> LOCATION:
<223> OTHER INFORMATION:
<300> PUBLICATION INFORMATION:

<400> SEQUENCE: 7 tctcc agcctctcac cgca                                              24

<210> SEQ ID NO 8
<211> LENGTH: 12
<212> TYPE: DNA
<213> ORGANISM: Bacillus globigii
<220> FEATURE:
<221> NAME/KEY:
<222> LOCATION:
<223> OTHER INFORMATION:
<300> PUBLICATION INFORMATION:

<400> SEQUENCE: 8 gcggt ga                                                           12

<210> SEQ ID NO 9
<211> LENGTH: 24
<212> TYPE: DNA
<213> ORGANISM: Bacillus globigii
<220> FEATURE:
<221> NAME/KEY: Fragment J Bgl 24
<222> LOCATION:
<223> OTHER INFORMATION:
<300> PUBLICATION INFORMATION:

<400> SEQUENCE: 9 cgtcg actatccatg aaca                                              24

<210> SEQ ID NO 10
<211> LENGTH: 12
<212> TYPE: DNA
<213> ORGANISM: Bacillus globigii
<220> FEATURE:
<221> NAME/KEY:
<222> LOCATION:
<223> OTHER INFORMATION:
<300> PUBLICATION INFORMATION:
```

```
<400> SEQUENCE: 10
gatctgttca tg                                                         12

<210> SEQ ID NO 11
<211> LENGTH: 24
<212> TYPE: DNA
<213> ORGANISM: Bacillus globigii
<220> FEATURE:
<221> NAME/KEY:
<222> LOCATION:
<223> OTHER INFORMATION:
<300> PUBLICATION INFORMATION:

<400> SEQUENCE: 11
aggcaactgt gctatccgag ggaa                                            24

<210> SEQ ID NO 12
<211> LENGTH: 12
<212> TYPE: DNA
<213> ORGANISM: Bacillus globigii
<220> FEATURE:
<221> NAME/KEY:
<222> LOCATION:
<223> OTHER INFORMATION:
<300> PUBLICATION INFORMATION:

<400> SEQUENCE: 12
gatcttccct cg                                                         12

<210> SEQ ID NO 13
<211> LENGTH: 24
<212> TYPE: DNA
<213> ORGANISM: Bacillus amyloliquefaciens
<220> FEATURE:
<221> NAME/KEY:
<222> LOCATION:
<223> OTHER INFORMATION:
<300> PUBLICATION INFORMATION:

<400> SEQUENCE: 13
agcactctcc agcctctcac cgag                                            24

<210> SEQ ID NO 14
<211> LENGTH: 12
<212> TYPE: DNA
<213> ORGANISM: Bacillus amyloliquefaciens
<220> FEATURE:
<221> NAME/KEY:
<222> LOCATION:
<223> OTHER INFORMATION:
<300> PUBLICATION INFORMATION:

<400> SEQUENCE: 14
gatcctcggt ga                                                         12

<210> SEQ ID NO 15
<211> LENGTH: 24
<212> TYPE: DNA
<213> ORGANISM: Bacillus amyloliquefaciens
<220> FEATURE:
<221> NAME/KEY:
<222> LOCATION:
<223> OTHER INFORMATION:
<300> PUBLICATION INFORMATION:

<400> SEQUENCE: 15
accgacgtcg actatccatg aacg                                            24
```

<210> SEQ ID NO 16
<211> LENGTH: 12
<212> TYPE: DNA
<213> ORGANISM: Bacillus amyloliquefaciens
<220> FEATURE:
<221> NAME/KEY:
<222> LOCATION:
<223> OTHER INFORMATION:
<300> PUBLICATION INFORMATION:

<400> SEQUENCE: 16
gatccgttca tg                                                              12

<210> SEQ ID NO 17
<211> LENGTH: 24
<212> TYPE: DNA
<213> ORGANISM: Bacillus amyloliquefaciens
<220> FEATURE:
<221> NAME/KEY:
<222> LOCATION:
<223> OTHER INFORMATION:
<300> PUBLICATION INFORMATION:

<400> SEQUENCE: 17
aggcaactgt gctatccgag ggag                                                 24

<210> SEQ ID NO 18
<211> LENGTH: 12
<212> TYPE: DNA
<213> ORGANISM: Bacillus amyloliquefaciens
<220> FEATURE:
<221> NAME/KEY:
<222> LOCATION:
<223> OTHER INFORMATION:
<300> PUBLICATION INFORMATION:

<400> SEQUENCE: 18
gatcctccct cg                                                              12

<210> SEQ ID NO 19
<211> LENGTH: 24
<212> TYPE: DNA
<213> ORGANISM: Haemophilus influenzae
<220> FEATURE:
<221> NAME/KEY:
<222> LOCATION:
<223> OTHER INFORMATION:
<300> PUBLICATION INFORMATION:

<400> SEQUENCE: 19
agcactctcc agcctctcac cgca                                                 24

<210> SEQ ID NO 20
<211> LENGTH: 12
<212> TYPE: DNA
<213> ORGANISM: Haemophilus influenzae
<220> FEATURE:
<221> NAME/KEY:
<222> LOCATION:
<223> OTHER INFORMATION:
<300> PUBLICATION INFORMATION:

<400> SEQUENCE: 20
agcttgcggt ga                                                              12

<210> SEQ ID NO 21
<211> LENGTH: 24

```
<212> TYPE: DNA
<213> ORGANISM: Haemophilus influenzae
<220> FEATURE:
<221> NAME/KEY:
<222> LOCATION:
<223> OTHER INFORMATION:
<300> PUBLICATION INFORMATION:

<400> SEQUENCE: 21
accgacgtcg actatccatg aaca                                              24

<210> SEQ ID NO 22
<211> LENGTH: 12
<212> TYPE: DNA
<213> ORGANISM: Haemophilus influenzae
<220> FEATURE:
<221> NAME/KEY:
<222> LOCATION:
<223> OTHER INFORMATION:
<300> PUBLICATION INFORMATION:

<400> SEQUENCE: 22
agcttgttca tg                                                           12

<210> SEQ ID NO 23
<211> LENGTH: 24
<212> TYPE: DNA
<213> ORGANISM: Haemophilus influenzae
<220> FEATURE:
<221> NAME/KEY:
<222> LOCATION:
<223> OTHER INFORMATION:
<300> PUBLICATION INFORMATION:

<400> SEQUENCE: 23
aggcagctgt ggtatcgagg gaga                                              24

<210> SEQ ID NO 24
<211> LENGTH: 12
<212> TYPE: DNA
<213> ORGANISM: Haemophilus influenzae
<220> FEATURE:
<221> NAME/KEY:
<222> LOCATION:
<223> OTHER INFORMATION:
<300> PUBLICATION INFORMATION:

<400> SEQUENCE: 24
agcttctccc tc                                                           12

<210> SEQ ID NO 25
<211> LENGTH: 24
<212> TYPE: DNA
<213> ORGANISM: Haemophilus parainfluenzae
<220> FEATURE:
<221> NAME/KEY:
<222> LOCATION:
<223> OTHER INFORMATION:
<300> PUBLICATION INFORMATION:

<400> SEQUENCE: 25
agcactctcc agcctctcac cgac                                              24

<210> SEQ ID NO 26
<211> LENGTH: 11
<212> TYPE: DNA
<213> ORGANISM: Haemophilus parainfluenzae
<220> FEATURE:
<221> NAME/KEY:
```

```
<222> LOCATION:
<223> OTHER INFORMATION:
<300> PUBLICATION INFORMATION:

<400> SEQUENCE: 26
cggtcggtga g                                                              11

<210> SEQ ID NO 27
<211> LENGTH: 24
<212> TYPE: DNA
<213> ORGANISM: Haemophilus parainfluenzae
<220> FEATURE:
<221> NAME/KEY:
<222> LOCATION:
<223> OTHER INFORMATION:
<300> PUBLICATION INFORMATION:

<400> SEQUENCE: 27
accgacgtcg actatccatg aaac                                                24

<210> SEQ ID NO 28
<211> LENGTH: 11
<212> TYPE: DNA
<213> ORGANISM: Haemophilus parainfluenzae
<220> FEATURE:
<221> NAME/KEY:
<222> LOCATION:
<223> OTHER INFORMATION:
<300> PUBLICATION INFORMATION:

<400> SEQUENCE: 28
cggtttcatg g                                                              11

<210> SEQ ID NO 29
<211> LENGTH: 24
<212> TYPE: DNA
<213> ORGANISM: Haemophilus parainfluenzae
<220> FEATURE:
<221> NAME/KEY:
<222> LOCATION:
<223> OTHER INFORMATION:
<300> PUBLICATION INFORMATION:

<400> SEQUENCE: 29
aggcaactgt gctatccgag ggac                                                24

<210> SEQ ID NO 30
<211> LENGTH: 11
<212> TYPE: DNA
<213> ORGANISM: Haemophilus parainfluenzae
<220> FEATURE:
<221> NAME/KEY:
<222> LOCATION:
<223> OTHER INFORMATION:
<300> PUBLICATION INFORMATION:

<400> SEQUENCE: 30
cggtccctcg g                                                              11

<210> SEQ ID NO 31
<211> LENGTH: 24
<212> TYPE: DNA
<213> ORGANISM: Haemophilus parainfluenzae
<220> FEATURE:
<221> NAME/KEY:
<222> LOCATION:
<223> OTHER INFORMATION:
<300> PUBLICATION INFORMATION:
```

-continued

```
<400> SEQUENCE: 31
acttctacgg ctgaattccg acac                                          24

<210> SEQ ID NO 32
<211> LENGTH: 12
<212> TYPE: DNA
<213> ORGANISM: Haemophilus parainfluenzae
<220> FEATURE:
<221> NAME/KEY:
<222> LOCATION:
<223> OTHER INFORMATION:
<300> PUBLICATION INFORMATION:

<400> SEQUENCE: 32
cggtgtcgga at                                                       12
```